United States Patent
Fincke

(10) Patent No.: US 6,671,545 B2
(45) Date of Patent: Dec. 30, 2003

(54) DEFIBRILLATOR WITH CONTROLLER OPERATING IN A LOW POWER MODE

(75) Inventor: Randall W. Fincke, Winchester, MA (US)

(73) Assignee: Cardiac Science, Inc., Irvine, CA (US)

( * ) Notice: Subject to any disclaimer, the term of this patent is extended or adjusted under 35 U.S.C. 154(b) by 0 days.

(21) Appl. No.: 10/227,698

(22) Filed: Aug. 26, 2002

(65) Prior Publication Data

US 2003/0032988 A1 Feb. 13, 2003

Related U.S. Application Data

(62) Division of application No. 09/652,054, filed on Aug. 31, 2000, now Pat. No. 6,546,285, which is a division of application No. 09/036,265, filed on Mar. 6, 1998, now Pat. No. 6,148,233.
(60) Provisional application No. 60/040,123, filed on Mar. 7, 1997.

(51) Int. Cl.[7] ................................. A61N 1/39
(52) U.S. Cl. ........................................ 607/5
(58) Field of Search ........................ 607/5–8

(56) References Cited

U.S. PATENT DOCUMENTS 4,202,340 A * 5/1980 Langer et al. .................. 607/5
5,330,504 A * 7/1994 Somerville et al. ............ 607/5

* cited by examiner

*Primary Examiner*—Jeffrey R. Jastrzab
(74) *Attorney, Agent, or Firm*—Gottlieb, Rackman & Reisman, P.C.

(57) ABSTRACT

A method of treating a patient for ventricular tachycardia using a wearable defibrillator includes monitoring the patient for a predetermined condition via one or more electrodes on the defibrillator, sending a message to the patient in response to the predetermined condition, activating the defibrillator so that the defibrillator delivers defibrillation energy to the patient, and storing at least one of the results of the monitoring, sending and activating steps in a memory on the defibrillator. The method also includes downloading information stored in the memory of the defibrillator to a base station having an external interface, and transmitting the information downloaded from the memory of the base station to an external location via the external interface of the base station.

25 Claims, 19 Drawing Sheets

DEFIBRILLATOR WITH CONTROLLER OPERATING IN A LOW POWER MODE

BACKGROUND OF THE INVENTION

This application is a division of U.S. Ser. No. 09/652,054 filed Aug. 31, 2000 now U.S. Pat. No. 6,546,285, which is a division to U.S. Ser. No. 09/036,265 filed Mar. 6, 1998 now U.S. Pat. No. 6,148,233 claiming priority to provisional application U.S. Ser. No. 60/040,123 filed Mar. 7,1997 incorporated herein be reference.

FIELD OF THE INVENTION

The present invention is directed to a defibrillation device, and more particularly to a personal wearable pacer/cardioverter/defibrillator which monitors a patient's condition, detects shockable or paceable arrhythmias, determines consciousness, and, in the case that the patient is determined to be unconscious, administers therapy to the patient.

DESCRIPTION OF THE RELATED ART

Cardiac arrhythmias, such as ventricular fibrillation and ventricular tachycardia, are electrical malfunctions of the heart, in which regular electrical impulses in the heart are replaced by irregular, rapid impulses. These irregular, rapid impulses can cause the heart to stop normal contractions, thereby interrupting blood flow therethrough. Such an interruption in blood flow can cause organ damage or even death.

Normal heart contractions, and thus normal blood flow, can be restored to a patient through application of electric shock. This procedure, which is called defibrillation, has proven highly effective at treating patients with cardiac arrhythmias, provided that it is administered within minutes of the arrhythmia. In the past, this was not always possible, since defibrillation units were large, and thus not easy to move, and could only be operated by an experienced clinician.

In response to the foregoing drawbacks of defibrillation units, implantable defibrillators were developed. Such defibrillators, however, also have several drawbacks. Specifically, use of a such a defibrillator requires surgery, thereby making their use inconvenient and even undesirable under certain circumstances. Moreover, implantable defibrillators are also costly, both in terms of the device itself and in terms of the cost of the surgery and subsequent treatments.

To address the foregoing drawbacks of implantable defibrillators, portable automatic external defibrillators (hereinafter "AEDs") were developed. These defibrillators are typically used by trained emergency medical system personnel. The major shortcoming of these defibrillators is the delay between the onset of ventricular fibrillation and the administering of a first shock. It has been estimated that survival decreases by 10% for each minute that passes after the first minute of ventricular fibrillation.

Temporary high risk patients who do not reach an ICD have little protection against sudden cardiac arrest ("SDA"), particularly with the discovery that anti-arrhythmia drugs have been proven to be less effective than a placebo. Accordingly, there exists a need for a defibrillator, preferably a portable, wearable defibrillator, which addresses the foregoing drawbacks of conventional defibrillators.

SUMMARY OF THE INVENTION

The present invention addresses the foregoing needs. For example, according to one aspect, the present invention is a defibrillator for delivering defibrillation energy to a patient. The defibrillator includes at least one electrode which attaches to the patient for transmitting the defibrillation energy to the patient and for receiving patient information from the patient, and a plurality of capacitors which are switchable so as to alter characteristics of the defibrillation energy. According to the invention, a controller controls switching of the plurality of capacitors in accordance with the patient information received from the at least one electrode.

By monitoring the patient for patient information and switching the plurality of capacitors in accordance with the patient information, the foregoing aspect of the invention makes it possible to deliver, to the patient, defibrillation energy which is appropriate for that patient. As a result, the invention provides increased effectiveness in the treatment of cardiac arrhythmias.

According to another aspect, the present invention is a way in which to increase long-term wear of a sensing electrode, such as a traditional defibrillation electrode (i.e., electrodes having a conductive surface area of over 60 $cm^2$), a low-surface-area electrode (i.e., electrodes having a conductive surface area of roughly 60 to 10 $cm^2$), or segmented electrodes (i.e., electrodes having a conductive surface area of roughly 8 to 10 $cm^2$). Specifically, the invention includes a variety of different techniques for increasing the amount of time that an electrode can be worn by a patient without resulting in substantial skin irritation or damage. For example, according to one embodiment, one or more electrodes are moved on the patient's body periodically. As another example, therapeutic or prophylactic agents are provided in or on the electrode. Also, the size, configuration, and materials used to construct the electrodes contribute the amount of time that the electrodes can be worn by a patient.

According to another aspect, the present invention is a defibrillator for delivering defibrillation energy to a patient. The defibrillator includes a signal generator for generating the defibrillation energy and a plurality of segmented electrodes each having a conductive area for transmitting the defibrillation energy to the patient. The plurality of segmented electrodes are divided into groups of two or more electrodes, each of the groups of electrodes having at least one line connected to the signal generator. Each of the lines has a length that is sufficient for each group of electrodes to be placed on the patient a predetermined distance away from others of the groups of electrodes. In the invention, the electrodes in at least one of the groups are spatially arranged to have an effective conductive area which is greater than a total combined conductive area of the electrodes in the group.

According to still another aspect, the invention is a segmented electrode device for use during ventricular fibrillation of a patient. The segmented electrode device includes a plurality of segmented electrodes each having a conductive area for transmitting defibrillation energy to the patient. The plurality of segmented electrodes are divided into groups of two or more electrodes, each of the groups of electrodes having at least one line connected to a signal generator. Each of the lines has a length that is sufficient for each group of electrodes to be placed on the patient a predetermined distance away from others of the groups of electrodes. In the invention, the electrodes in at least one of the groups are spatially arranged to have an effective conductive area which is greater than a total combined conductive area of the electrodes in the group.

By virtue of the electrode configurations in the foregoing two aspects of the invention, it is possible to simulate a larger conductive area using segmented electrodes. As a result, these aspects of the invention have an advantage over their conventional counterparts. That is, these aspects of the invention are able to provide defibrillation energy to the patient without using large electrodes. Thus, these aspects of the invention provide reduced skin irritation without a corresponding reduction in efficacy.

According to another aspect, the present invention is a defibrillator for delivering defibrillation energy to a patient. The defibrillator includes an external interface, over which patient information is transmitted to an external location, and a patient interface, over which the defibrillation energy is transmitted to the patient, and over which the patient information is received. A processor is included in the defibrillator, which analyzes the patient information received over the patient interface and which controls transmission of the defibrillation energy to the patient based on at least a first portion of the patient information. A memory stores at least a second portion of the patient information prior to transmission of the second portion of the patient information over the external interface.

By controlling transmission of the defibrillation energy to the patient based on at least a first portion of information received from the patient, the invention is able to tailor the defibrillation energy to the patient's needs. Moreover, because the invention includes a memory which stores at least a second portion of the patient information, and includes an external interface over which such information may be transmitted, the invention is capable of recording patient information, such as patient electrocardiogram (hereinafter "ECG") information or the like for a period of time, and of transmitting that patient information to an external location, such as a central repository, hospital, doctor, etc.

According to another aspect, the present invention a defibrillator for delivering defibrillation energy to a patient. The defibrillator includes a processor and a patient interface, over which patient information is received from the patient and over which the defibrillation energy is transmitted to the patient. The processor operates in a normal mode and a low-power consumption mode, wherein, during the normal mode, the processor receives the patient information and controls transmission of the defibrillation energy in accordance with the patient information.

By having the processor operate in a low-power consumption mode, the invention reduces the amount of power consumed by the defibrillator. As a result, a power supply will last longer in the defibrillator of the present invention than in its conventional counterparts.

According to another aspect, the present invention is a defibrillation system which includes a defibrillator for delivering defibrillation energy to a patient and a base station connected to the defibrillator. The defibrillator includes a plurality of electrodes connected to the patient for transmitting defibrillation energy to the patient and for receiving patient information from the patient, and a memory which stores the patient information and defibrillation information, the defibrillation information relating to operation of the defibrillator. The defibrillator also includes a base station interface, over which the patient information and the defibrillation information are transmitted, and over which external information is received, and a controller for controlling when the defibrillation energy is transmitted to the patient based on the patient information and at least part of the external information. The base station includes a defibrillator interface which mates to the base station interface of the defibrillator and over which (i) the defibrillation information and the patient information is received from the memory of the defibrillator, and (ii) the external information is transmitted to the defibrillator. The base station also includes an external interface, over which the defibrillation information and the patient information is transmitted to an external location, and over which the external information is received from the external location.

By virtue of the foregoing arrangement, it is possible to transmit patient and defibrillation information from a defibrillator to a base station and from the base station to an external location, such as a central repository, doctor, hospital, etc. Moreover, the foregoing arrangement makes it possible to transmit external information from the base station to the defibrillator. This external information can be used, e.g., to reprogram the defibrillator, to alert a patient to a possible condition in the patient or the defibrillator, etc. In particularly preferred embodiments of the invention, a memory on the defibrillator containing patient and defibrillation information is removable, and can be transferred to the base station or to an external location for downloading.

According to another aspect, the present invention is a defibrillation system which includes a defibrillator for delivering predetermined defibrillation energy to a patient, an indicator which indicates operational defects in the defibrillator, and a base station which is interfaced to the defibrillator. The base station performs diagnostics on the defibrillator in order to detect operational defects in the defibrillator, and transmits results of the diagnostics to the defibrillator. The indicator provides an indication of such operational defects in the defibrillator when the base station detects operational defects in the defibrillator.

By alerting the patient to operational defects in the defibrillator while the defibrillator is still in the base station, this aspect of the invention is able to reduce the chances of malfunction following a cardiac arrhythmia. As a result, this aspect of the invention increases the patient's chances of surviving an arrhythmia.

According to another aspect, the present invention is a method of treating a patient for ventricular tachycardia, bradycardia, ventricular fibrillation, or other treatable rhythm using a pacer/converter/defibrillator in accordance with the present invention (hereinafter referred to solely as a "defibrillator"). The method includes monitoring the patient for a predetermined condition via one or more electrodes on the defibrillator, sending a message to the patient in response to the predetermined condition, activating the defibrillator so that the defibrillator delivers defibrillation energy to the patient, and storing at least one of the results of the monitoring, sending and activating steps in a memory on the defibrillator. The method also includes downloading information stored in the memory of the defibrillator to a base station having an external interface, and transmitting the information downloaded from the memory of the base station to an external location via the external interface of the base station.

By sending a message to the patient in response to the predetermined condition, by processing the patient's response, and by other consciousness detection methods, the present invention is able to reduce the chances of defibrillation energy being delivered to the patient while the patient is still conscious. Moreover, the foregoing aspect of the invention is able to store at least some information relating to the arrhythmia and the patient's response thereto, and to download that information to a base station, from whence the information may be transmitted to an external location for analysis or the like.

In this regard, according to another aspect, the present invention is a base station for use with a defibrillator. The base station includes a defibrillator interface over which information is exchanged with the defibrillator, an external interface over which information is exchanged with an external entity, and a controller. The controller (i) receives patient information and defibrillation information from the defibrillator, (ii) transmits the patient information and defibrillation information to the external entity, (iii) receives defibrillator programming information from the external entity, (iv) programs the defibrillator in accordance with the defibrillator programming information, (v) performs diagnostics on the defibrillator, and (vi) transmits results of the diagnostics to at least one of the defibrillator and the external entity.

Thus, the base station of the present invention may both act as an interface between a defibrillator and an external entity and provide a patient with a means to ensure proper operation of the defibrillator.

According to another aspect, the present invention is a method for reprogramming a defibrillator based on a central database of information relating to patients that use a type of defibrillator. The method includes collecting, in the central database, information relating to a plurality of patients that use the type of defibrillator, analyzing the information stored in the central database so as to test an algorithm for detecting irregular heart activity, and correcting the algorithm for detecting irregular heart activity based on a result of the analyzing process. The method also includes transmitting a corrected algorithm to a plurality of base stations corresponding to the plurality of patients, and reprogramming a defibrillator in each of the base stations using the corrected algorithm.

By providing a way in which to test algorithms for detecting irregular heart activity, a way in which to correct such algorithms, and a way in which to reprogram a defibrillator with a corrected algorithm, the present invention is able to improve its performance over time.

In preferred embodiments, the invention features a long-term cardiac monitoring and defibrillation system that is wearable by a patient. The system includes at least two electrode arrays electrically connected to a portable defibrillator. The electrode arrays are spatially separated and adhered to portions of the patient's skin in the thoracic window area for an extended period of time, such that electrical activity of the heart can be monitored and effective defibrillation and/or pacing impulses can be delivered to the patient's heart. The electrode arrays comprise plural electrodes which are capable of sensing the patient's heart condition by detecting the electrical activity of the heart, and of delivering defibrillation or pacing impulses to the patient's heart when required.

In another aspect, the cardiac monitoring and defibrillation system of the invention comprises features which enhances the long-term wearability of the system. These features include use of a low-current defibrillation waveform and electrodes having a composition and/or geometric design adapted to minimize the area of the electrodes. In this regard, it has been determined that use of a lower current than that typically used for defibrillation can provided effective defibrillation, particularly when coupled with electrode arrays having electrode surface areas which are significantly smaller than the surface area of conventional defibrillation electrodes. The use of reduced area electrodes minimizes irritation to the skin. These features also permit higher impedance materials to be used in the electrodes, which is also less irritating to the patient's skin.

In one aspect, the electrode array comprises multiple spatially separated electrodes separated by non-conductive material, passive material or free space. The use of multiple smaller electrodes minimizes the electrode area in contact with the skin needed to deliver an effective defibrillation impulse to the heart, thereby reducing the area of skin in contact with electrode materials.

Another aspect of the invention features a long term cardiac monitoring and defibrillation system and method that ameliorates, reduces or prevents irritation of the patient's skin caused by delivery of defibrillation impulses and/or by the constant contact of the electrodes with the skin. According to this aspect skin that becomes irritated from contact with the electrodes is permitted to recover by periodically detaching the electrode arrays and moving or rotating them by a predetermined amount, and re-affixing either the same or new electrode arrays to different portions of the skin within the patient's thoracic window area. This moving or rotating allows substantially different sections of the patient's skin to be in contact with the electrodes so that portions of the skin previously in contact with the electrodes are allowed to recover.

The electrode arrays of the present invention preferably are designed for long term patient wearability. To this end, the electrode arrays include a therapeutic or prophylactic material which ameliorates, reduces or prevents irritation to the patient's skin in contact with the electrode arrays. Therapeutic or prophylactic materials may include, for example, wound healing agents, moisturizers, emollients, protective agents or antibacterial agents. Each electrode array comprises electrically conductive areas (electrodes) and electrically non-conductive areas (passive areas). The electrodes are capable of sensing the electrical activity of the heart, delivering electrical impulses (cardio and defibrillation) to the heart, as well as tactile stimulation and pacing signals.

The electrode arrays preferably include an adhesive portion for adhering the array directly to the skin. However, external means for retaining the electrode arrays in electrical proximity to the skin may be used, such as a vest or a band. Long term wearability of the electrode arrays may be enhanced by selecting materials for use in the electrode array which minimize irritation to the skin in contact with the array. Such materials may include, for example, adhesives and backing materials having a high moisture vapor transmission rate and conductive materials for use in the electrodes having low salt (ionic) concentrations or comprised of silicone or other adhesive materials that are conductive by means of additives.

In another embodiment, long term wear can be enhanced and skin irritation reduced by including in the system means for monitoring, and adjusting as necessary, the environment at the interface between the electrode array and the skin. Such means may include, for example, means for monitoring and adjusting the {PH at the skin-electrode interface in order to maintain a neutral non-irritating interface; and means for controlling the ion flow at the interface between the electrodes and the skin. In the latter embodiment, ion flow would be reduced to a minimum except for the short time during which a defibrillating shock is being delivered, at which time the ion flow would temporarily increase to provide a conductive path for the defibrillation impulse.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

FIG. 4 shows the layout of FIGS. 14A–14C.

DETAILED DESCRIPTION OF THE PREFERRED EMBODIMENTS

Figure 1:
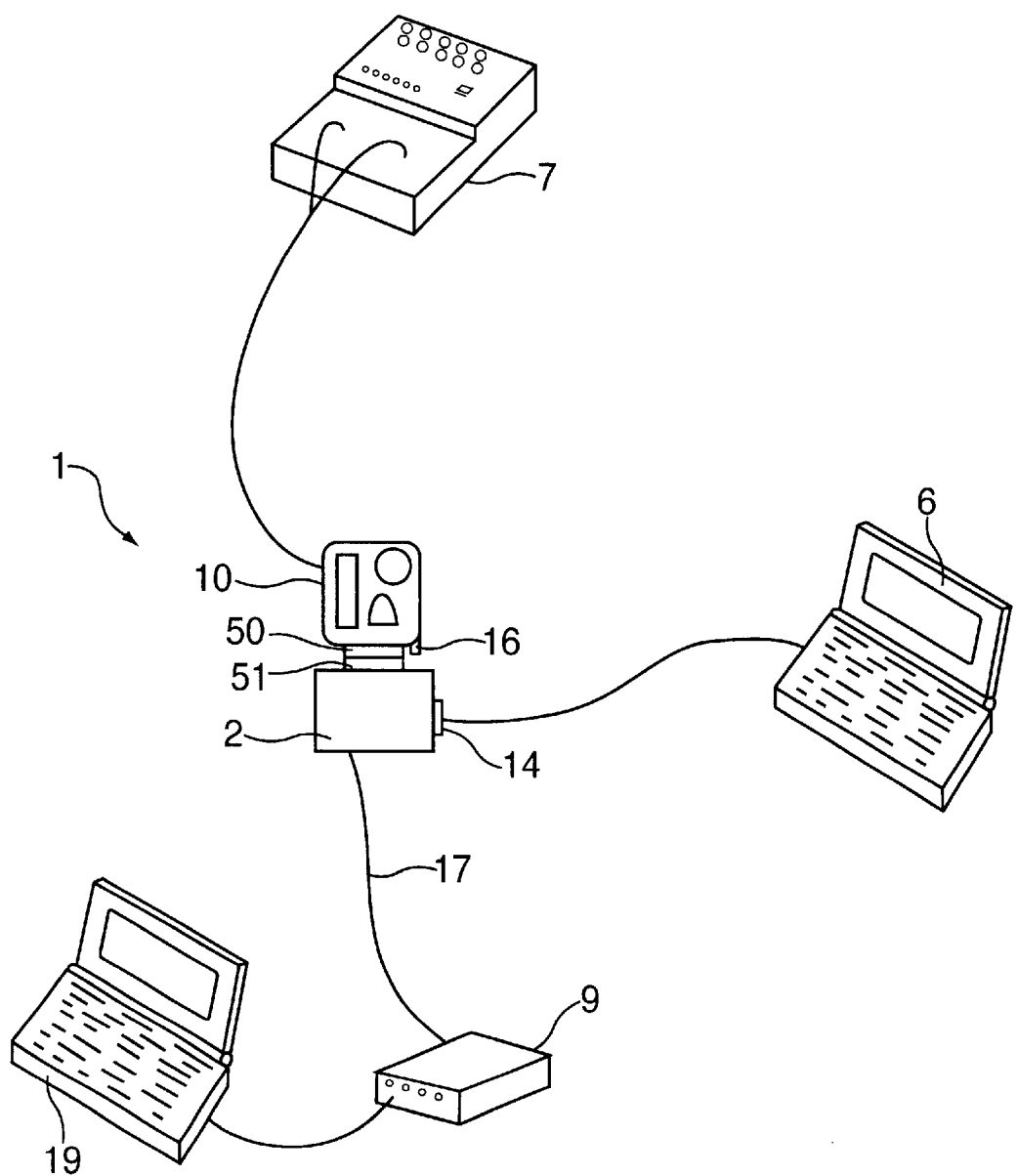
FIG. 1 shows a defibrillation system according to the present invention in a configuration for performing diagnostics and data uploading.
Figure 2:
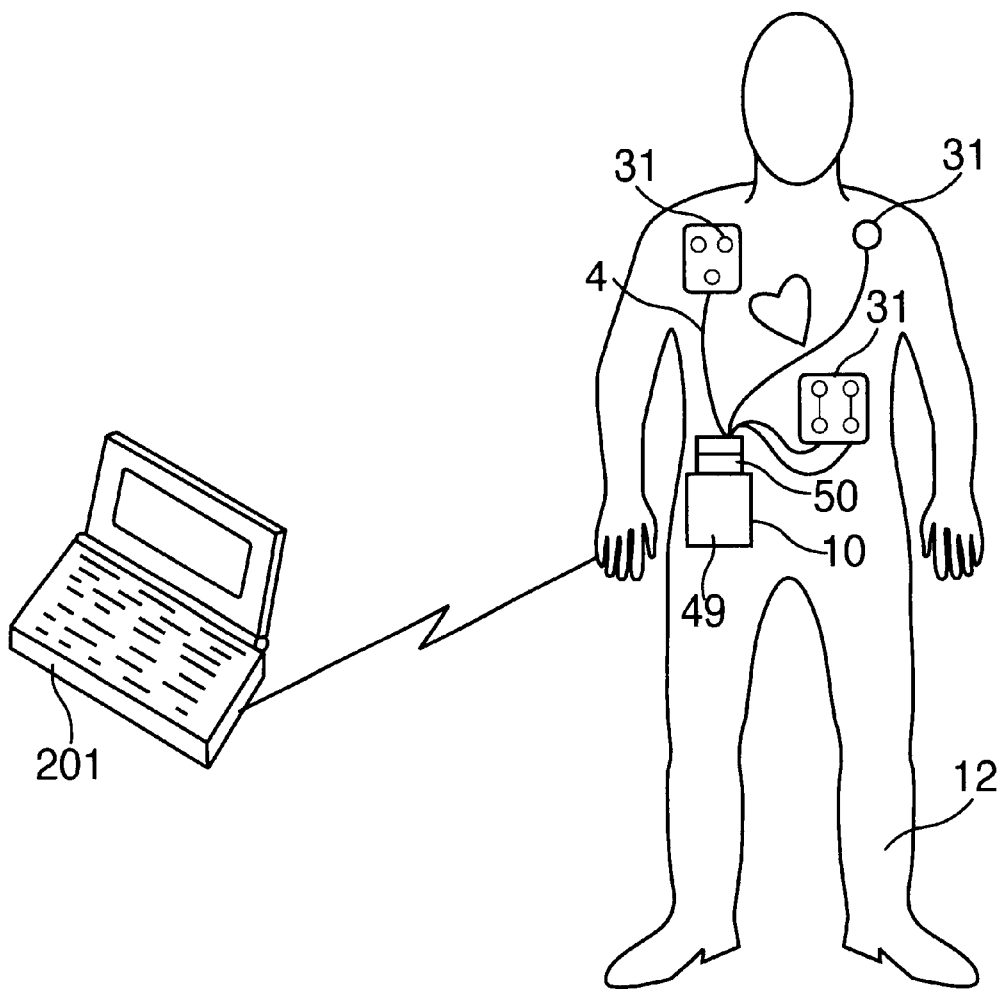
FIG. 2 shows the defibrillation system according to the present invention during use in connection with monitoring and treating a patient.

The present invention is directed to a defibrillation system for use in treating patients who have suffered from cardiac arrhythmias. A representative embodiment of the invention is shown in FIGS. 1 and 2. As shown in these figures, defibrillation system 1 is comprised of base station 2, electrode harness 4, personal computer 6, patient simulator 7, central repository 9, and wearable defibrillator 10. A brief overview of the operation of each of these components is provided below, followed by detailed descriptions thereof.

Defibrillator 10 is capable of interfacing either to base station 2, as shown in FIG. 1, or to electrode harness 4, as shown in FIG. 2. To this end, both electrode harness 4 and base station 2 include physical connector identifiers at their respective interfaces to defibrillator 10. By reading these connector identifiers, defibrillator 10 is able to determine both the type of interfaced device (i.e., a base station or electrode harness) and the identity of a particular interfaced device (i.e., one electrode harness as opposed to another), and then to react accordingly Electrode harness 4 includes one or more sensing electrodes 31 which interface to patient 12, and which are used both to monitor the patient and to transmit defibrillation energy to the patient. In this regard, although defibrillator 10 may be utilized with non-segmented electrodes having a low surface area or with traditional defibrillation electrodes, sensing electrodes 31 comprise segmented electrodes since these require the most description. Defibrillation energy, which can comprise an electric signal having a bi-phasic waveform, a mono-phasic waveform, or a truncated exponential waveform, is generated by defibrillator 10 in the event that predetermined conditions have been detected in the patient. These predetermined conditions include whether the patient has suffered a cardiac arrhythmia, whether the patient is conscious, as well as other conditions, such as patient impedance, that are monitored by sensing electrodes 31.

Defibrillator 10 is also capable of providing pacing impulses and tactile stimulation signals to the patient via electrode harness 4. The tactile stimulation signals alert the patient to abnormal cardiac activity in the patient, whereas the pacing impulses stimulate contractions of the patient's heart. While electrode harness 4 is being worn by the patient, data may be transmitted directly from defibrillator 10 to personal computer 201 via non-contact interface 16.

When defibrillator 10 is interfaced to base station 2, as shown in FIG. 1, base station 2 is able to perform diagnostics on the defibrillator, to reprogram the defibrillator, and to retrieve data stored in the defibrillator. Such data can include an operational history of the defibrillator, information concerning the patient's cardiac activity, and the like. All or some of this retrieved data may be transmitted, via personal computer interface 14, to personal computer 6 for display and/or processing.

Data retrieved by base station 2 from defibrillator 10 may be transmitted to central repository 9 via external data link 17. Central repository 9 preferably stores this data, together with patient and defibrillation information corresponding to a plurality of other patients, all of whom use the same type of defibrillator. A personal computer 19 is in communication with central repository 9. This personal computer may be used to analyze the patient and defibrillation information received from defibrillator 10 in view of corresponding information from the plurality of other patients, and, if desired, to provide the results of this analysis back to base station 2.

As shown in FIG. 1, defibrillator 10 also includes a link to patient simulator 7. Patient simulator 7 comprises test equipment which simulates bodily functions and characteristics of a patient, including cardiac activity and thoracic impedance. During testing, defibrillator 10 monitors patient simulator 7 in much the same way that defibrillator 10 monitors a patient and, in a case that predetermined conditions have been detected in patient simulator 7, transmits defibrillation energy to patient simulator 7. To aid in the testing process, patient simulator 7 also simulates patient responses to the defibrillation energy provided by defibrillator 10 and provides response information back to defibrillator 10. This response information may be transmitted to, and analyzed by, base station 2, and then provided to any one or more of central repository 9, computer 6, or defibrillator 10.

Electrode Harness

Figure 3:
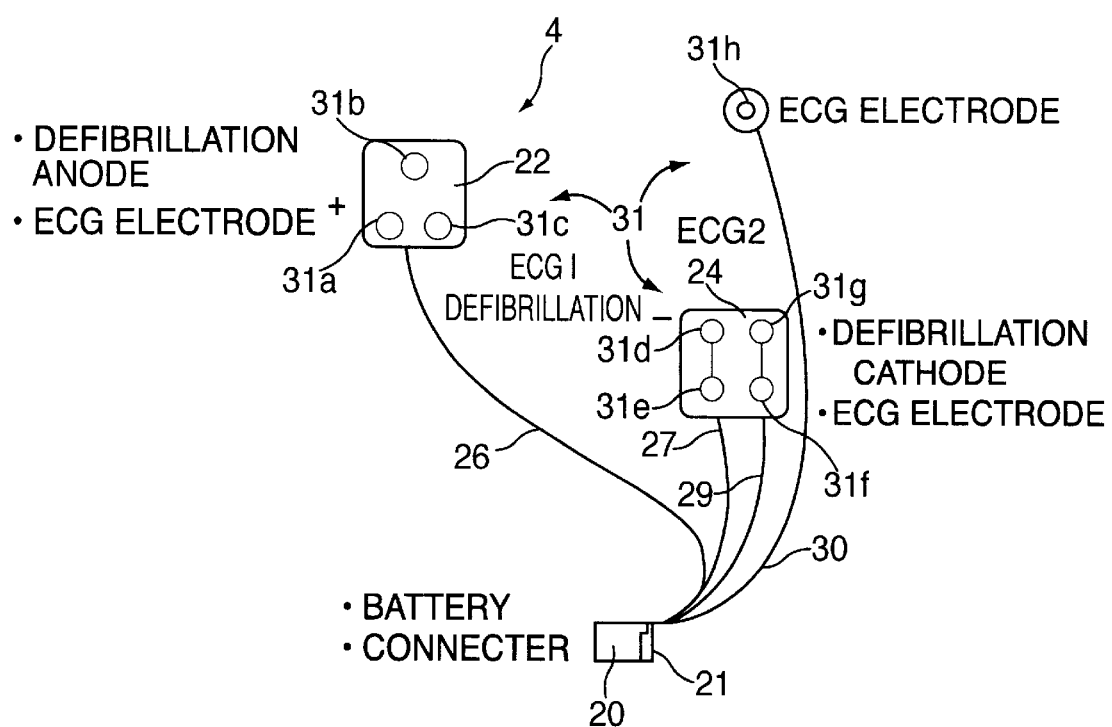
FIG. 3 shows an electrode harness used with the defibrillation system of FIGS. 1 and 2.

FIG. 3 shows a close-up view of electrode harness 4. Electrode harness 4 is preferably disposable and, in preferred embodiments of the invention, can be worn for approximately 2 to 7 days or longer for a cumulative period of 1 week to 12 months. To this end, electrode harness may include a means for defibrillator 10 to determine how long electrode harness 4 has been connected thereto. For example, in one embodiment of the invention, electrode harness 4 includes an identification resistor (not shown) as its physical connector identifier. Defibrillator 10 measures the resistance across this resistor and then starts a countdown, after which defibrillator 10 notifies the patient that it is time to change the electrode harness. In this regard, each electrode harness may include a different, unique resistance associated therewith. Defibrillator 10 may measure this resistance by passing a current therethrough and, in this manner, determine the identity of an interfaced electrode harness.

As shown in FIG. 3, electrode harness 4 includes power supply 20, connector 21, non-electrically conductive padding 22 and 24, electrical leads (or "lines") 26, 27, 29 and 30, and sensing electrodes 31. Sensing electrodes 31 comprise the defibrillator's interface to the patient. Specifically, sensing electrodes 31 attach to the patient so as to monitor the patient, transmit tactile stimulation energy, and to transmit defibrillation energy to the patient under appropriate circumstances. Each electrode may comprise a single layer of conductive material. In preferred embodiments of the invention, however, each electrode is multi-layered as shown, for example, in the cross-sectional view of electrode 31*a* in FIG. 4. In the example shown in FIG. 4, electrode 31*a* includes three layers, namely top cover assembly 32, conductor/wire assembly 33, and skin interface 32.

Skin interface 32 contacts directly with the patient's skin and comprises a layer of material, such as a hydrogel, that is capable of transmitting defibrillation energy to the patient without causing substantial irritation or harm to the skin. For larger patients, or hypoallergenic patients, conductive screens or meshes can be used in addition to or in place of hydrogel. These screens or meshes may be used in combination with a cream, such as a hydrating cream or a skin healing cream. Such creams also may be applied to the patient's skin before attaching the electrodes thereto.

Skin interface 32 contacts to conductor/wire assembly 34, which can be either substantially coextensive with, or smaller than, skin interface 32. Conductor/wire assembly 34 includes conductive layer 34*a*, wire connection 34*b*, wire 34*c*, and sealing layer 34*d*. Conductive layer 34*a* preferably comprises a silver/silver chloride polymer base ink silkscreened onto a layer of Tyvek (used as an insulator and as a carrier) which is die-cut and folded. A wire with a welded washer is then attached to conductive layer 34*a* by means of a washer (tin plated nickel) and eyelet (a hollow rivet that is crimped in order to hold the assembly together). Insulating tape is then wrapped around this connection in order to reduce corrosion.

As an alternative to the silver/silver chloride formulation, conductor 34*a* may comprise conductive metal such as tin, silver, gold, copper, salts or oxides of these conductive metals, carbon, a substrate which has been coated with a conductive compound (e.g., polytetrafluoroethylene), an ink silkscreened on a carrier, metallized cloth, solid metal or carbon grid, foil, plate, etc. Conductor 34 preferably has a thickness which is sufficient to transmit at least ten successive defibrillation energy singals having peak amplitudes of 23 amperes for a duration of 10.75 msec each.

Top cover assembly 33 includes foam insulating layer 33*a* and wearable adhesive layer 37. Adhesive 37, which can comprise an adhesive material fixed to a backing, such as tape or the like, is disposed adjacent to conductor 34 and/or skin interface 32 and is used to attach electrode 31*a* to the patient's skin. In preferred embodiments of the invention, adhesive 37 may also be temperature sensitive, meaning that adhesion thereof increases or decreases in response to temperature variations. Adhesive 37 is preferably non-conductive.

Adhesive 37 should also be adapted for long-term wear. To this end, an adhesive having a high moisture vapor transmission rate ("MVTR") of approximately 300 to 1500 $g/m^2/day$ is suitable for use with the invention. By virtue of this feature of the invention, the adhesive is made breathable, meaning that it permits air to be transmitted therethrough to the patient's skin. This increases the amount of time an electrode may be worn without causing substantial harm to the patient's skin. Adhesive 37 should also be sufficient to adhere to the patient's body in the face of normal movements or muscle contractions and in the face of normal water exposure such as might occur during bathing or sweating. However, adhesive 37 should not be so strong as to cause substantial discomfort during removal of an electrode. To this end, adhesive 37 preferably has a peel strength of 500 g/cm or less.

Figure 4:
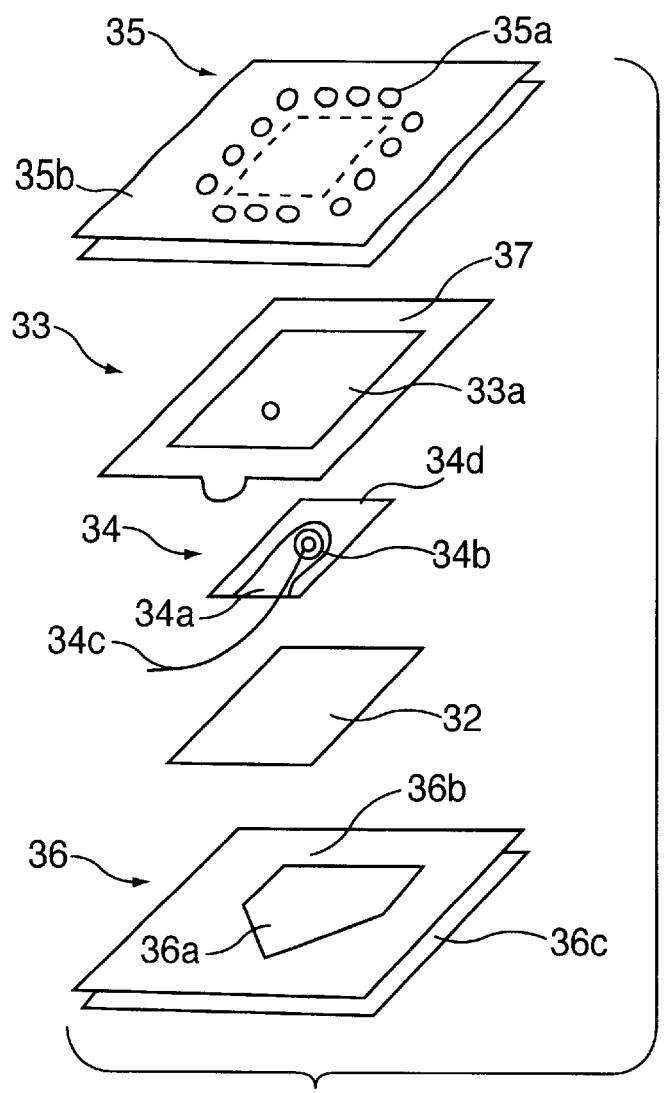
FIG. 4 shows a view of a sensing electrode and applicator used in the electrode harness of FIG. 3.

Also shown in FIG. 4 are applicator 35 and release liner assembly 36. Applicator 35 includes two layers—a bottom layer having cut-outs 35*a* and a top layer having an adhesive 35*b*. Cut-outs 35*a* limit the amount of adhesive that contacts the top side of the electrode. Release liner assembly 36 includes cut-out 36*a* on upper layer 36*b* (closest to the hydrogel) which causes only a portion of urethane bottom layer 36*c* to come into contact with upper layer 36*b*. This configuration of release liner assembly 36, particularly cut-out 36*a*, allows bottom layer 36*c* to be removed first from an electrode, followed by upper-layer 36*b*, without causing any separation of the electrode from the applicator assembly. Moreover, cut-outs 35*a* on applicator 35*b* facilitate removal of applicator 35*b* from top cover assembly 35 without causing harm to the electrode.

Figure 18:
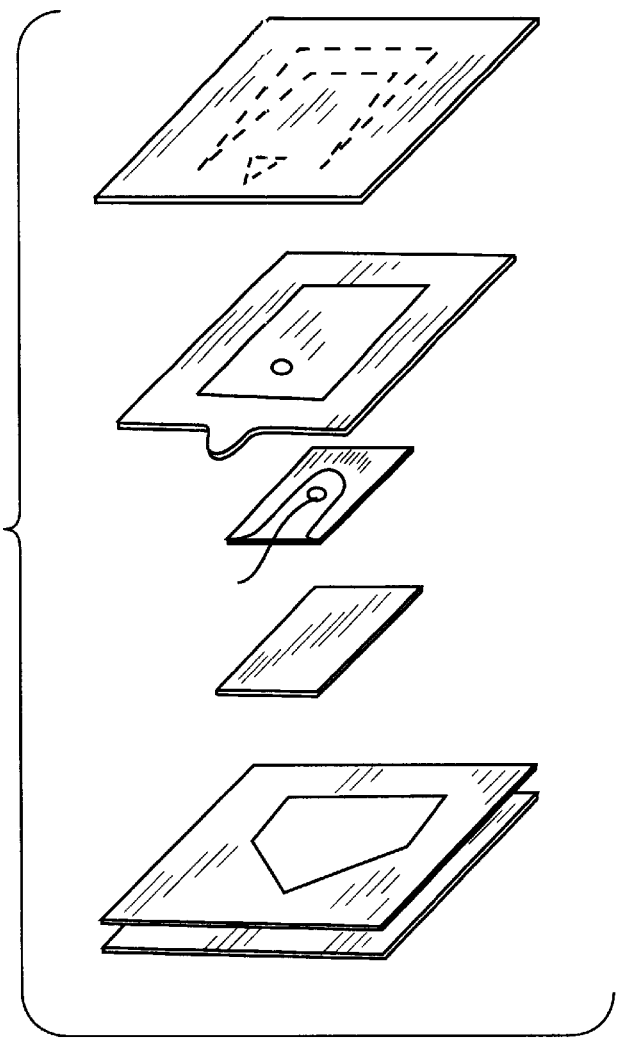
FIG. 18 shows a view of an alternative electrode and applicator configuration that may be used in the present invention that uses selectively applied adhesives in the applicators.
Figure 19:
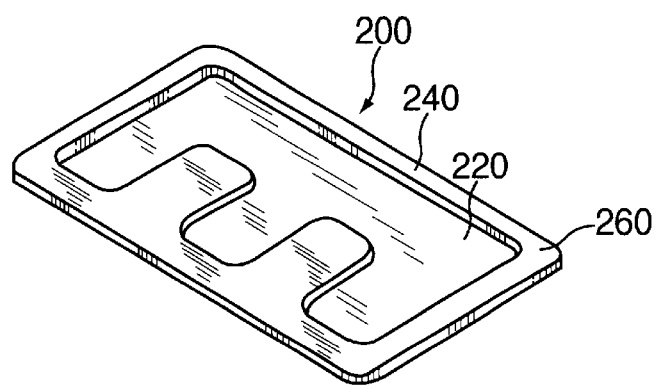
FIG. 19 is a view of an alternative electrode configuration that may be used in the present invention.

An alternative electrode configuration to that shown in FIG. 4 is shown in FIG. 18. FIGS. 19 to 24 show additional alternative electrode configurations. FIG. 19 shows a finger-patterned electrode 200 comprising a conductive adhesive polymer layer 220, a carbon sheet 240, and a medical adhesive carrier 260, covering and extending beyond the edges of the polymer layer 220 and the carbon sheet 240. In other embodiments, a metal sheet or a metal fabric may replace carbon sheet 220.

Figures 20A, 21A:
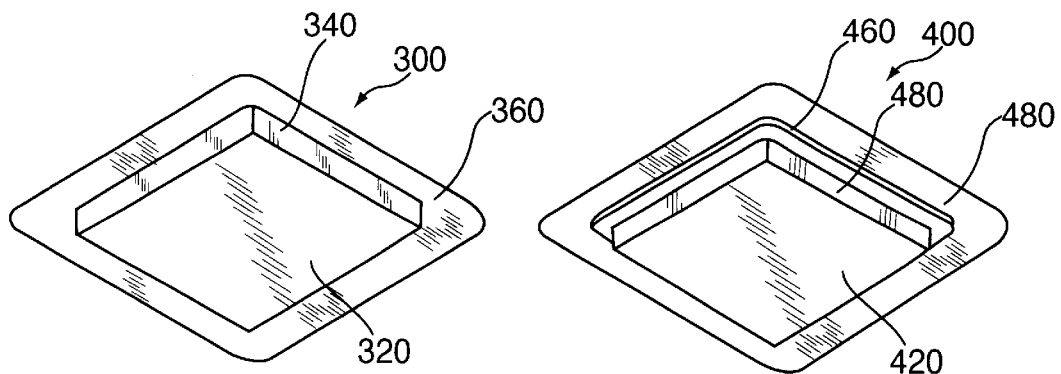
FIGS. 20A and 20B are views of an alternative electrode configuration that may be used in the present invention.
FIGS. 21A and 21B are views of an alternative electrode configuration that may be used in the present invention.
Figures 20B, 21B:
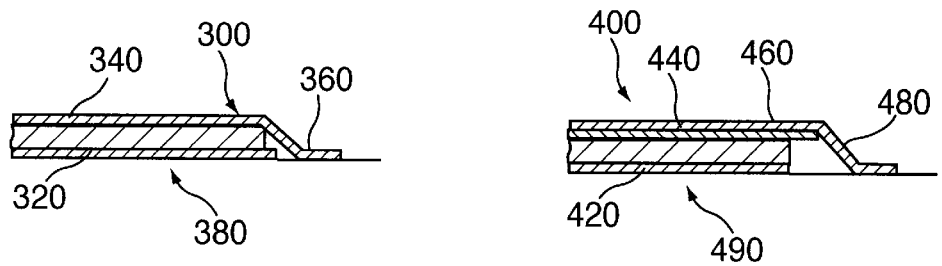

FIG. 20A and FIG. 20B show a rectangular electrode 300 comprising metal foil sheet 320, pressure pad backing 340 and medical adhesive carrier 360, covering and extending beyond the edges of the metal foil sheet 320 and the pressure pad backing 340. The front surface of metal foil sheet 320 comes in contact with patient's skin 380 and pressure pad backing 340 contacts the back surface of metal foil sheet 320 and keeps metal foil sheet 320 in close contact with skin 380. In this regard, a pressure pad is a unit which can be deformed by pressure applied in the direction perpendicular to the skin. By maintaining a thickness that is less than a free dimension, pressure in the pad is assured. Medical adhesive carrier 360 contacts pressure pad backing 340. In another embodiment, a metal fabric replaces metal foil sheet 320.

FIGS. 21A and 21B show rectangular electrode 400 comprising metal foil sheet 420, pressure pad backing 440, stiffener 460, and medical adhesive carrier 480. The front surface of metal foil 420 is in contact with skin 490; the front surface of pressure pad 440 is in contact with the back surface of metal foil 420; the front surface of stiffener 460 is in contact with the back surface of pressure pad 440; and medical adhesive carrier 480 is in contact with stiffener 460 and covers and extends beyond the edges of all other layers (420, 440, and 460). Stiffener 460 comprises a material which will resist bending, and stiffener 460 is used to transmit force into the electrode area. In a preferred embodiment, stiffener 460 comprises a thin plastic material with an area that is slightly larger than areas of metal foil sheet 420 and pressure pad backing 440. In another embodiment, a metal fabric replaces metal foil sheet 420.

Figures 22, 23:
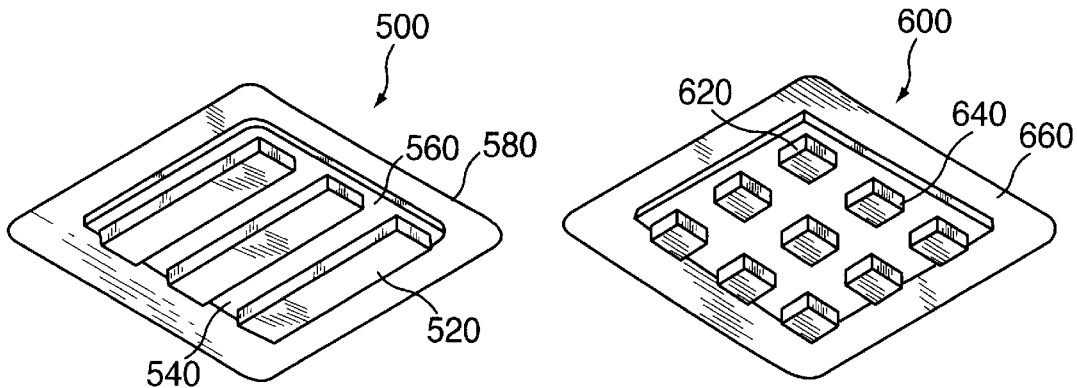
FIG. 22 shows a view of an alternative electrode configuration that may be used in the present invention.
FIG. 23 shows a view of an alternative electrode configuration that may be used in the present invention.

FIG. 22 shows electrode 500 with alternating strips of active areas 520 and space 540 for breathing. Each active area 520 comprises a metal foil sheet and a pressure pad backing. The strips of active areas 520 are in contact with stiffener 560, and stiffener 560 is in contact with medical adhesive carrier 580. In another embodiment, a metal fabric replaces the metal foil in each active area 520. In yet other embodiments each active area comprises a metal foil sheet or a metal fabric, a pressure pad backing and a stiffener. The back surfaces of the active areas are in contact with a medical adhesive carrier.

FIG. 23 show electrode 600 with multiple small square-shaped active areas 620. As in the alternative strip configuration, active areas 620 are spaced for breathing. Each active area 620 comprises a metal foil and a pressure pad backing. The back surfaces of active areas 620 are in contact with the front surface of stiffener 640, and medical adhesive carrier 660 is in contact with the back surface of stiffener 640. In another embodiment, a metal fabric replaces the metal foil sheet. In yet other embodiments, each active area comprises a metal foil sheet or a metal fabric, a pressure pad backing and a stiffener. Back surfaces of the active areas are in contact with a medical adhesive carrier.

Figure 24:
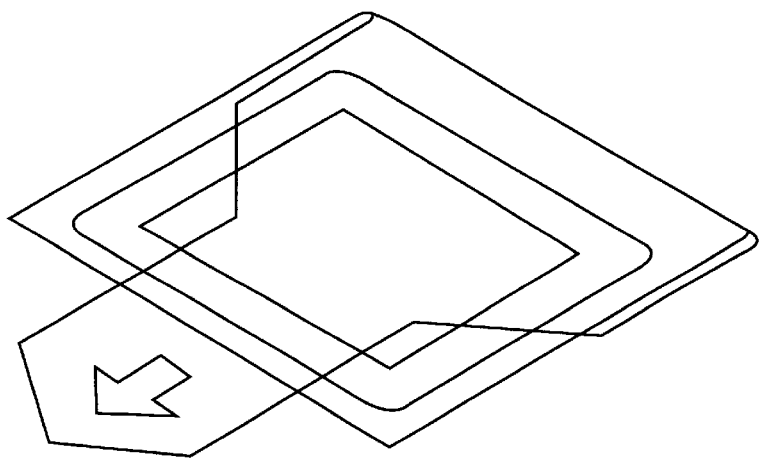
FIG. 24 shows an embodiment of an electrode in which an adhesive surface is covered with a pull-tab covering to allow the patient to place the electrode on the patient's skin and then to pull the tab to expose the adhesive surface.

FIG. 24 shows an embodiment of the electrode in which the adhesive surface is covered with a pull-tab covering to allow the patient to place the electrode on the skin and then pull the tab to expose the adhesive surface and maintain the electrode in place.

A conductive portion of each sensing electrode, which in this case are segmented electrodes, preferably has a surface area that is roughly 8 to 10 $cm^2$; although other dimensions may be used. The present invention, however, takes advantage of "spreading resistance" in the patient's bodily tissue so as to permit this reduction in the surface area of the conductive portion each electrode. Spreading resistance is a property of human tissue which causes defibrillation energy (or any other electric signal for that matter) applied to the patient's skin to spread outward over the skin and downward and outward through the patient's tissue. In the context of the present invention, once current from the defibrillation energy is applied from an electrode to the patient's skin, the current diffuses beyond the electrode and continues to diffuse as the current moves into the underlying tissue. As a result of this diffusion, the density of the current decreases with increasing distance from the perimeter of the electrode. The present invention compensates for this by placing sensing electrodes 31 in a geometric pattern such that the interaction between diffusing current from each sensing electrode results in an accumulation of spreading current in areas between sensing electrodes 31. The result is that an effective area is created in which current densities in the path between groups of sensing electrodes (e.g., sensing electrodes 31a, 31b and 31c shown in FIG. 3) are similar to that of a large electrode having a perimeter equal to an outer perimeter of all of the sensing electrodes in the group. A similar effect may be achieved through random placement of the electrodes on the patient.

Thus, by spatially arranging the sensing electrodes to take advantage of human tissue's spreading resistance, the present invention is able to create a "virtual" conductive surface using relatively small electrodes. The virtual conductive surface can be significantly larger than a combined conducive area of the individual sensing electrodes. This also contributes to a lower impedance for a combined surface area of the sensing electrodes than would be the case for a continuous electrode having a similar surface area.

Each of sensing electrodes 31 may be shaped so that the conductive portion thereof has a perimeter which is greater than a circumference corresponding to a radius of the electrode. That is, since charge tends to migrate to the perimeter of an electrode, the present invention attempts to maximize the perimeter of each electrode, particularly conductive surfaces thereof, thereby increasing the amplitude of the defibrillation energy that the electrode can handle without causing substantial burns to the patient. Examples of electrodes with such a perimeter include star-shaped electrodes, square electrodes, swirled-shaped electrodes, etc. It is, however, noted that conventional circular electrodes may be used in conjunction with the present invention as well.

To increase operational efficiency of sensing electrodes 31, sensing electrodes 31 should be placed within a "thoracic window" on the patient's body. A thoracic window is defined as an area of the patient's body which is suitable for placing electrodes so as to optimize delivery of defibrillation energy to the patient's heart, and is described in an article by Geddes et al. the American Heart Journal, volume 94, page 67 (1977), the contents of which are hereby incorporated by reference into the subject application as if set forth herein in full. In this regard, there are two currently defined thoracic windows on a patient. These comprise the anterior-posterior thoracic window and the apex-sternum thoracic window. In the apex-sternum thoracic window, electrodes are typically placed underneath the patient's left rib cage and over the patients right shoulder area. In the anterior-posterior thoracic window, electrodes are typically placed on a patient's lower left back and left front. Preferably, the sensing electrodes are placeable over the thoracic window either randomly or in a geometric pattern which is sufficient to cover a large enough area of the patient's myocardium to cause adequate defibrillation upon application of defibrillation energy.

Electrodes 31 can be attached or placed in contact with the skin by various methods. Proper defibrillation requires that the electrodes be in close contact with the patient's skin, in addition to being placed in an appropriate location within the patient's thoracic window area. Preferably, the electrode are attached to the patient's skin using an adhesive thereon, as described in more detail below. However, other attachment means are possible. For example, a thoracic wrap made out of cotton or spandex can be used to assure proper placement of the electrodes and good contact between the electrodes an the skin.

In order to ensure proper current accumulation in areas between the sensing electrodes, each sensing electrode in a group (e.g., the group of electrodes 31a, 31b and 31c) should be placed within a predetermined distance of other sensing electrodes in the group. In preferred embodiments of the invention, each sensing electrode in each group of electrodes is separated from other sensing electrodes in that same group by between 0.5 and 3 times an effective diameter of each electrode, where the effective diameter corresponds to the farthest distance between two points on the electrode. To ensure proper separation among the sensing electrodes, electrode harness 4 includes non-electrically conductive pads 22 and 24 (i.e., the passive areas), on which groups of sensing electrodes can be mounted in predetermined geometric configurations. For example, as shown in FIG. 3, sensing electrodes 31a, 31b and 31c (i.e., the active areas) are mounted on pad 22 in a triangular configuration, while sensing electrodes 31d, 31e, 31f and 31g are mounted on pad 24 in a rectangular configuration. Although FIG. 3 shows only two geometric arrangements for sensing electrodes 31, the invention is not limited to these. Rather, any geometric arrangement may be utilized, including, but not limited to, a checkerboard pattern, swirl patterns, interlocking patterns, star patterns, crescent patterns, E-shaped patterns, F-shaped patterns, L-shaped patterns, X-shaped patterns, H-shaped patterns, O-shaped patterns, C-shaped patterns, etc. Of course, the electrodes may be arranged in a random manner as well.

Figure 5:
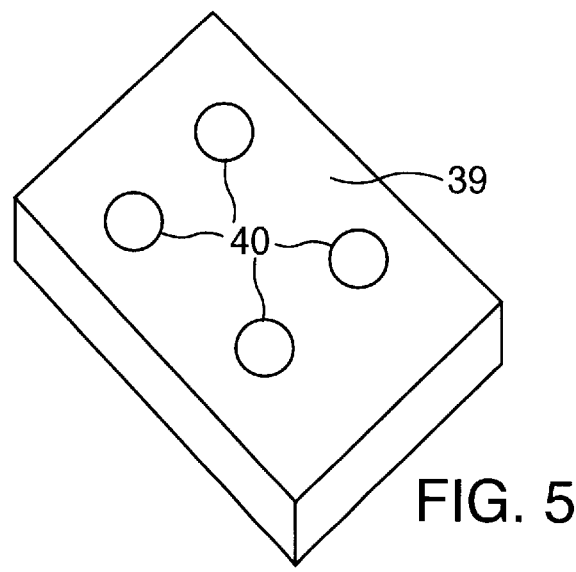
FIG. 5 shows an application tray used to apply sensing electrodes to a patient's body.

Preferably, pads 22 and 24 are flexible so as to facilitate placement of sensing electrodes 31 on contours of the patient's body. It is noted, however, that pads 22 and 24 need not be flexible. Rather, an adhesive tape can be used in place of pads 22 and 24 or, alternatively, in addition to pads 22 and 24. As still another alternative, pads 22 and 24 can be used selectively in electrode harness 4, meaning that pads can be used to mount some of sensing electrodes 31 and not others. In fact, this is the case in the representative embodiment of the invention depicted in FIG. 3. That is, in the embodiment shown in FIG. 3, segmented electrodes is not mounted on a pad, but rather "floats", meaning that it can be mounted anywhere on a patient's body, constrained, of course, by the length of its electrical lead 30. As described below, electrode 31h does not provide the defibrillation energy to the patient, but rather is used only to monitor the patient's ECG. However, to provide greater flexibility in electrode placement, in alternative embodiments of the invention, all electrodes may float in the same manner as sensing electrode 31h. In the case that all or some electrodes float, the invention may include an applicator tray, such as tray 39 shown in FIG. 5, having cups 40 which arrange the electrodes in geometric pattens so as to ensure accurate placement within the patient's thoracic window. That is, the applicator tray ensures that the electrodes will be spatially arranged in the manner described above so as to take advantage of human tissue's spreading effect.

As noted above, electrodes 31 may include a hydrogel or other conductive material on a surface thereof which comes into contact with the patient's skin, i.e., on the skin interface of the electrode. The hydrogel is electrically conductive, thereby permitting transmission of the defibrillation energy to the patient, but has a relatively low ion concentration that is low enough so as to not to cause substantial skin irritation.

In preferred embodiments, the conductivity of the hydrogel is variable based, e.g., on temperature, etc. In addition, the hydrogel preferably has a relatively high MVTR, thereby making the hydrogel breathable. As was the case above with respect to adhesive 37, this reduces skin irritation caused by wearing the electrodes, and thus increases the amount of time that the electrodes can be worn.

Hydrogels or other conductive materials used with conventional ECG electrodes may be used in the present invention, since the deleterious effects of such materials will be countered by the present invention for reasons described both above and below. In addition, conductive materials which meet the above qualifications include electrolytes, such as sodium chloride (NaCl), potassium chloride (KCl), or lithium chloride (LiCl). Currently preferred hydrogel materials include hydrophilic polymers, such as karaya gum, gum acacia, locust bean gum, polysaccharide gum, modified polysaccharide, or polyacrylamide. A hydrating agent, such as water or polyhydric alcohol (e.g., glycerine, propylene glycol, triethylene glycol, glycerol, etc.) may also be included in the conductive material. In these cases, water is typically present at a concentration from about 1% to 60% by weight, whereas polyhydric alcohol is typically present at a concentration from about 10% to 50% by weight.

As noted above, the electrode interface to the skin may include, instead of or in addition to a hydrogel, a mesh, screen, or other porous material. These elements are conductive and, due to their porous nature, allow air to pass therethrough to the patient's skin. As was the case with the hydrogel described above, this feature of the invention provides for prolonged wearability of the electrodes.

The hydrogel on each sensing electrode may also include a therapeutic or prophylactic agent which reduces skin irritation caused by the electrode, and/or which promotes healing of wounds or skin irritation that may be caused by the sensing electrodes. Such an agent may be applied directly to each electrode, or capsules which release the agent in response to the defibrillation energy may be applied to the electrode. A therapeutic or prophylactic agent may also be included on each of pads 22 and 24 in order to promote skin health. Agents which render the patient's skin porous, such as keratolytic agents (e.g., salicylic acid) or rubefacient (e.g., methyl salicylate) may be included on each electrode or pad so as to facilitate transmission of the therapeutic or prophylactic agent into the skin and/or to permit use of low water content hydrogels.

Examples of therapeutic or prophylactic agents that may be used with the present invention include moisturizers, emollients, bactericides, mold inhibitors, stabilizers or buffers to maintain a neutral PH and to reduce corrosion and skin sensitivity, gelation inhibitors (e.g., $Mg(OAc)_2$), healing agents, hormonal agents (e.g., hydrocortisone (steroids)), protective agents, etc. Examples of acceptable bactericides and mold inhibitors include antibactierals, antiseptics, antifungals, boric acid, bacitracin, acriflavine, formaldehyde, gentian violet, mercuric sulfide, mercurochrome, neomycin, and iodine. Examples of acceptable stabilizers include oligo or polybasic organic acids and their salts (including chelating agents), polyethers, tartaric acid, citric acid, and n-alkyl sulfonate, where n is from 8 to 16 carbon atoms. Examples of acceptable healing agents include allantoin, peruvian balsam, vitamin A, and vitamin B. Examples of acceptable protective agents include benzoin, charcoal, talc, zinc oxide, and aloe vera. These therapeutic agents may be used both prior to use or after use to promote healing.

The amount of therapeutic or prophylactic material used corresponds to an amount effective to reduce irritation, or to promote recovery of irritated skin. The therapeutic or prophylactic agent may be in any form useful to achieve the intended purpose, including liquid solutions, creams, gels, solids, granules, powders or any other form, including microcapsules. As noted above, the therapeutic or prophylactic agent may be included as part of the electrode, e.g., incorporated in the conductive areas of the electrode, or incorporated in a passive area of the electrode array. Alternatively, the electrode array may comprise three areas: electrode areas, passive areas and areas containing the therapeutic or prophylactic material. In addition, the therapeutic or prophylactic material may be applied to the skin prior to attaching the electrodes (pre-treatment), or after the electrodes have been removed (post-treatment). In another embodiment, skin irritation may be reduced by including in the electrode array means for monitoring, controlling and/or correcting the skin environment in contact with the electrode array. For example, it is possible to monitor the electrode-to-skin PH, and adjust the PH accordingly. Along these lines, the electrodes may comprise a multi-layered matrix for controlling ion flow between the skin and the electrode.

In alternative embodiments of the invention, rather than using the sensing electrode configuration described above, i.e., segmented electrodes, non-segmented electrodes having conductive portions of less than 60 cm$^2$ and, in some cases, even to less than 30 cm$^2$ may be utilized. In this regard, traditionally, it was necessary for conductive portions of defibrillation electrodes to have a surface area of 60 cm$^2$ to 80 cm$^2$ in order to deliver a sufficient defibrillation energy to the patient. The present invention, however, takes advantage of the "spreading resistance" effect described above so as to permit reduction in the surface area of each electrode. Of course, the features described herein with respect to sensing electrodes 31 may also be used in conjunction with the non-segmented electrodes described herein. These features include, but are not limited to, using hydrogels having low ion concentrations, therapeutic and prophylactic agents, and/or high MVTRs, effecting electrode movement relative to the patient so as to reduce the deleterious effects of electrode-to-skin contact, etc., utilizing an adhesive designed for long-term wear, etc. As well, the following monitoring and energy-transmitting functions described with respect to segmented electrodes may also be used in conjunction with the non-segmented electrodes described herein.

In still other embodiments of the invention, traditional non-segmented defibrillation electrodes, i.e., electrodes having a surface area of 60 cm$^2$ to 80 cm$^2$, may be used in conjunction with all aspects of the invention described herein, particularly those aspects of the invention that provide for long term (i.e., greater than two days) wearability of the electrodes. In this regard, these aspects include, but are not limited to, using the electrodes in conjunction with hydrogels having low ion concentrations, therapeutic and prophylactic agents, and/or high MVTRs, effecting electrode movement relative to the patient so as to reduce the deleterious effects of electrode-to-skin contact, etc., utilizing an adhesive designed for long-term wear, etc. As well, the following monitoring and energy-transmitting functions described with respect to sensing electrodes 31 may also be used in conjunction with the traditional non-segmented electrodes described herein.

It is noted that defibrillator 10 may also be used with any type of commercially-available subcutaneous electrode as well. It is still further noted that the invention may include combinations of two or more of the foregoing types of electrodes.

Referring back to FIG. 3, in electrode harness 4, each group of electrodes and/or single electrode has at least one electrical lead mechanically connected between its lead interface and power supply 20. The leads can be standard cables comprising electrically conductive wires sheathed in a flexible, protective material, e.g., a flexible plastic material. The wires used in the leads preferably are able to carry repeated defibrillation impulses of at least 20 A for a 20 millisecond duration, and preferably have adequate insulation qualities satisfying a high potential test for about 1750 V. In addition, the cables preferably are flexible, durable, soft and comfortable while having sturdy insulation.

Figure 17:
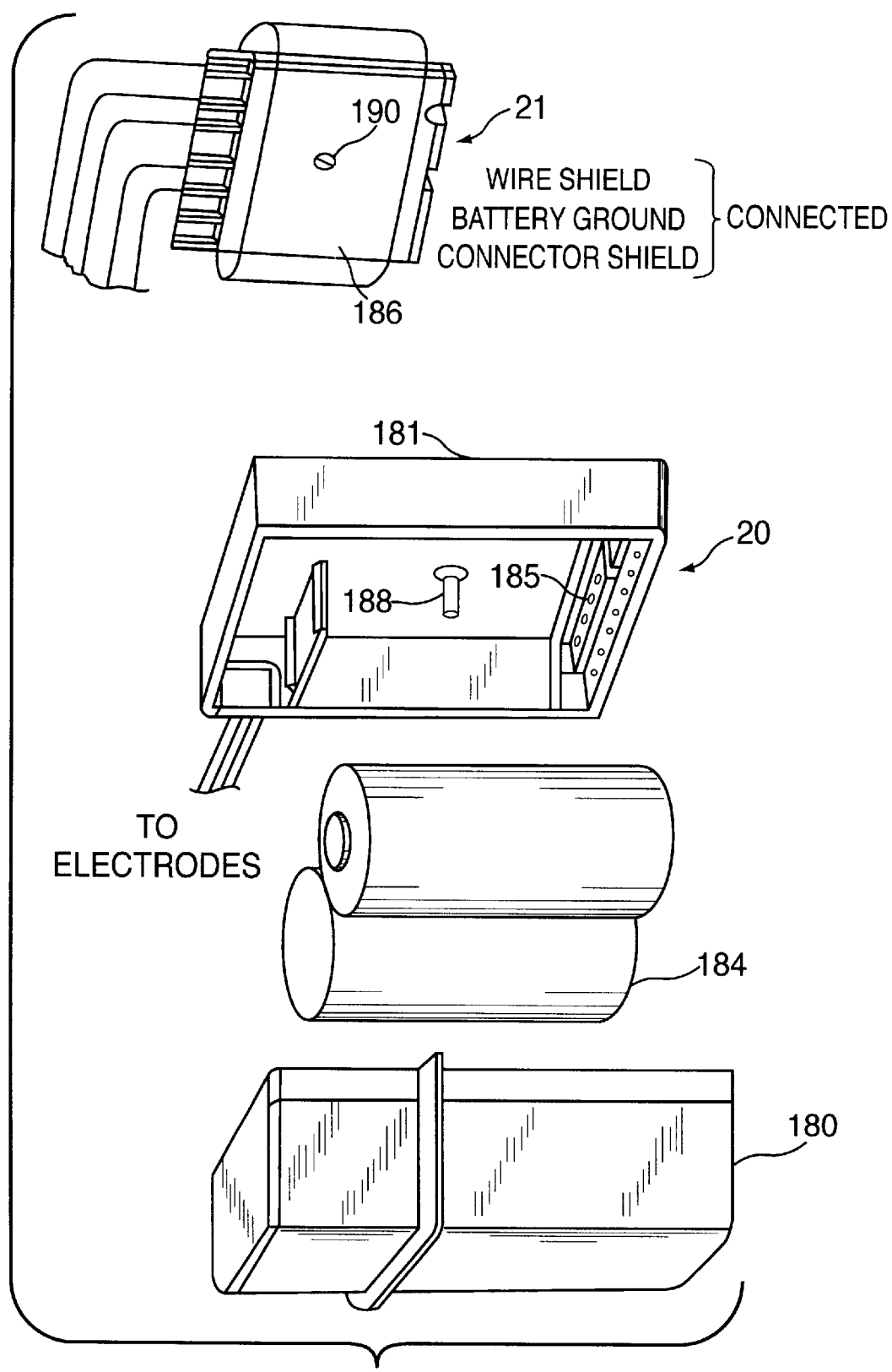
FIG. 17 is an exploded view of the primary power supply used in the defibrillator of the present invention.

An exploded view of power supply 20 is shown in FIG. 17. As shown in FIG. 17, power supply 20 includes base 180, top 181 and, sandwiched therebetween, batteries 184. Power supply 20 is also comprised of connector 21, which includes the physical connector identifier for electrode harness 4, and which interfaces power supply 20 and electrical leads 26, 27, 29 and 30 to defibrillator 10. To this end, connector 21 includes socket 186 which receives the electrical leads via holes 185. Socket 186 fits within top 181 such that pin 188 on top 181 contacts with hole 190 on socket 186. Socket 186 is shielded so as to protect signals being transmitted therethrough from batteries 184. This shielding is tied to the "floating" ground in the battery and also to shields from the leads to the electrodes.

In preferred embodiments of the invention, each electrical lead is non-removably connected to connector 21 on power supply 20, meaning that each lead is hard-wired to connector 21 or is otherwise connected to connector 21 in a way in which removal of the electrical leads from connector 21 will damage either one or both of these components. It is noted, however, that alternative embodiments of the invention are possible, in which each lead is removably connected to connector 21.

Power supply 20 comprises the primary power cell for wearable defibrillator 10. To this end, batteries 184 comprise non-rechargeable lithium batteries (e.g., DL123A, size 2/3 A) which are capable of providing 2 to 7 days of normal operation of defibrillator 10, including delivering at least six defibrillation energy (i.e., shocks) having peak currents of 23 A to the patient. In this regard, the working voltage of power supply 20 is preferably 3.3 to 6.6 V, with the maximum output being 6.6 V.

In preferred embodiments, power supply 20 is made water-resistant by sealing power supply 20 within a silicone membrane (not shown) or the like. In this regard, power supply 20 may be made water-resistant by a number of other means as well. For example, it is possible to use a variety of other insulating materials in place of silicone. By sealing power supply 20 in this manner, it is possible to reduce the risk of unintended electric shock during activities, such as showering or the like.

Each electrical lead on electrode harness 4 has a length that is sufficient for each corresponding electrode or group of electrodes to be placed on the patient at a predetermined distance away from others of the electrodes or groups of electrodes. As noted above, by spatially arranging defibrillator (as opposed to solely ECG) electrodes in this manner, the invention ensures proper accumulation of current in areas between the sensing electrodes. The present invention provides an additional advantage in this regard in that groups of electrodes arranged in geometric patterns on the patient are movable relative to the patient in a manner which ensures that the geometric patterns are substantially retained, but are at different orientations relative to the patient. For example, it is possible to rotate pad 22 containing sensing electrodes 31a, 31b and 31c on a patient such that pad 22 is still within the patient's thoracic window (e.g., either the apex-sternum thoracic window, the anterior-posterior thoracic window, or some combination thereof), but such that sensing electrodes 31a, 31b and 31c do not contact the patient's skin at the same location. Random rotation or movement may also be used to accomplish the same result. For example, in a case that electrodes 31 all float, random motion may be the best way in which to achieve the desired result. Moreover, in accordance with the invention, and particularly with non-segmented electrodes, it is possible merely to shift each electrode from a first position to a second position, such that portions of the first and second positions overlap.

By providing for the foregoing rotation and/or movement, together with the therapeutic and prophylactic agents described above, the present invention reduces skin damage which may occur due to prolonged use of wearable defibrillator 10. To achieve optimum reduction in skin damage, each sensing electrodes 31, group of sensing electrodes, or individual non-sensing electrodes should be rotated in the above manner roughly once every 12 hours to 7 days.

In operation, sensing electrodes 31 are capable of transmitting electrical signals from defibrillator 10 to a patient. These electrical signals include, but are not necessarily limited to, defibrillation energy, tactile stimulation signals, pacing signals, and AC and DC signals used to measure a patient's skin and thoracic impedance. The same information used to measure the patient's thoracic impedance may also be used to determine the patient respiration and pulse rates. The defibrillation energy preferably has a bi-phasic waveform with two phases. These phases may have substantially equal durations or, alternatively, may have different durations, e.g., the first phase may be roughly 6 msec and the second phase may be roughly 4 msec. An example of a bi-phasic waveform having substantially equal durations is shown in FIG. 6 (described below).

Figure 6:
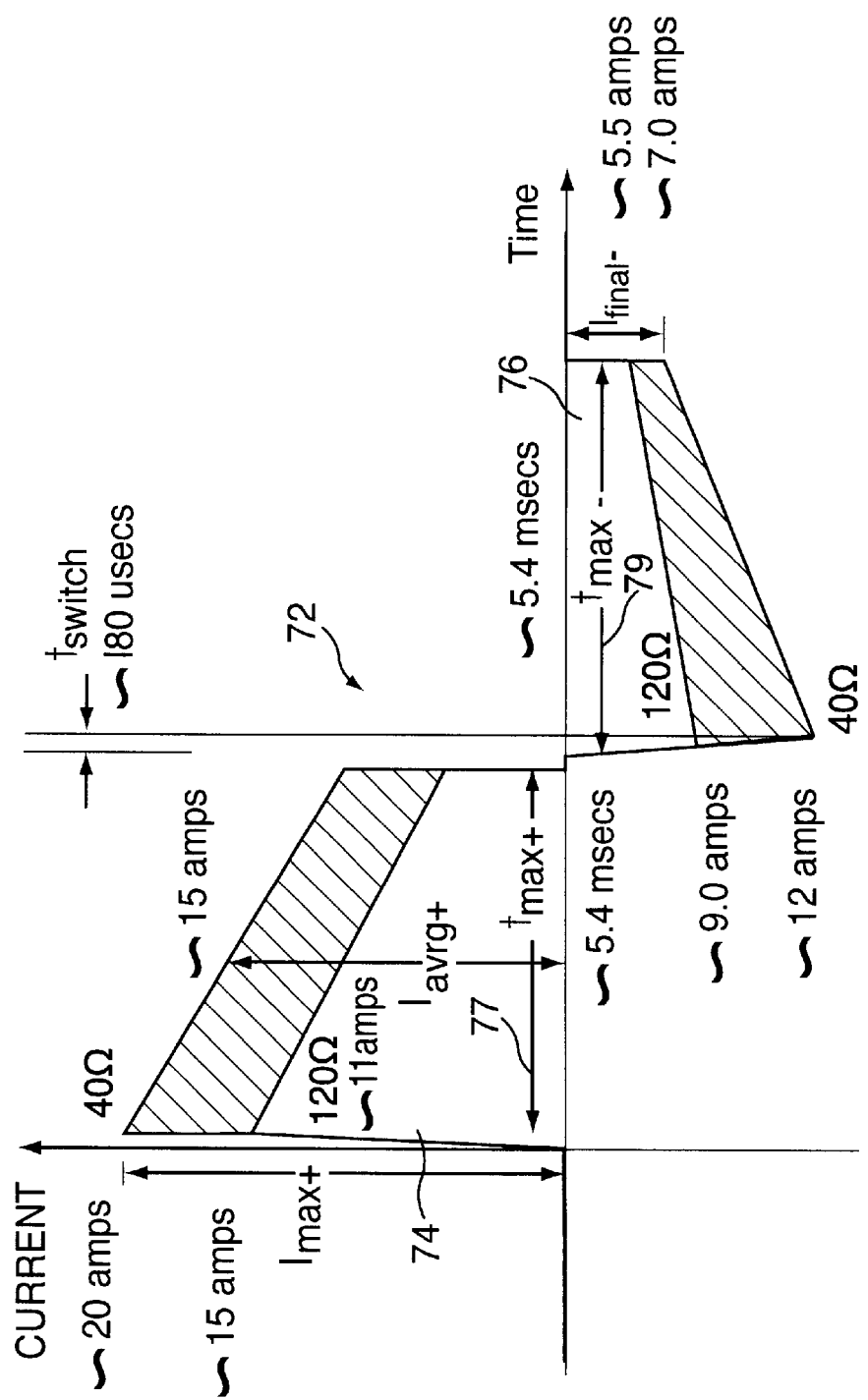
FIG. 6 shows defibrillation energy having a bi-phasic waveform which is generated by the defibrillation system of the present invention.

As noted above, the waveform of the defibrillation energy may also be mono-phasic, i.e., the waveform may comprise just the first one of the two phases shown in FIG. 6, or may comprise a truncated exponential waveform. Monophasic waveforms typically require greater current, generally on the order of 15% to 20% greater, in order to achieve substantially the same effect as bi-phasic waveforms. Regarding the pacing impulses, these preferably comprise waveforms having a low peak current of roughly 150 mA.

Sensing electrodes 31 are also capable of transmitting patient information from the patient to defibrillator 10. This patient information includes, but is not limited to, information relating to the patient's skin and thoracic impedance, artifact noise in the patient's body (caused, e.g., by cardiopulmonary resuscitation, agonal breathing, seizures, patient handling, and ambulatory or vehicular motion), sensory stimulation signals from the patient, and the patient's ECG, including any cardiovascular signals evidencing abnormal heart activity.

In this regard, electrode harness 4 preferably includes two independent differential channels, namely "ECG 1" and "ECG 2" shown in FIG. 3, for measuring the patient's ECG. In this regard, groups of electrodes 31a, 31b and 31c and 31d, 31e, 31f and 31g comprising ECG 1 both provide the defibrillation energy to the patient and monitor the patient's ECG, whereas electrode 31h comprising ECG 2 is used solely for monitoring the patient's ECG. ECG 1 serves as the primary monitoring channel for ECG analysis, whereas ECG 2 serves as a backup for use in a case that ECG 1 is not operating or is not operating properly (e.g., if ECG 1 is relatively noisy). Alternatively, ECG 2 can be used as a means of verifying the validity of an ECG obtained via ECG 1. That is, by comparing ECGs obtained from ECG 1 an ECG 2, it is possible to confirm the validity of the patient's ECG. It is also possible to confirm whether the electrodes are properly attached to the patient based on this comparison. As still another alternative, it is possible to "average" ECGs from ECG 1 and ECG 2, in order to obtain an averaged ECG for the patient, or to increase ECG resolution by using inputs from both ECG 1 and ECG 2. The use to which defibrillator 10 puts the ECG signal, as well as the other signals obtained via an electrode harness 4, is provided in detail below.

For example, defibrillator 10 provides several ways to measure the patient's thoracic impedance based on information received from sensing electrodes 31. Specifically, the patient's impedance is determined directly by applying an AC or DC signal through an electrode, sampling data obtained from the electrode in response to the AC or DC signal, and analyzing the sampled data. More specifically, in preferred embodiments of the invention, this method of measuring the patient's thoracic impedance entails sampling such data from an electrode within 5 seconds of defibrillator power-on and then every 10 seconds for a 160 msec period at a sample rate of 4 msec or to continuously sample the impedance signal. Filtering is then performed on the sampled data so as to reduce the bandwidth of the sampled data to less than 10 Hz. The sampled data is then analyzed so as to provide a noise magnitude estimate for the signal and a frequency content of the signal. Subsequent processing is then performed to obtain a measurement of the patient's thoracic impedance by averaging all of the data samples in each 160 msec period. This averaging and filtering is performed in order to reduce the effects of artifact noise associated with CPR, muscle tremors, and agonal breathing. Of course, this processing occurs in defibrillator 10, and not in electrode harness 4.

In addition to the foregoing method, the patient's thoracic impedance is also calculated by defibrillator 10 each time the defibrillation energy is transmitted to the patient. Specifically, the patient's thoracic impedance may be determined before, during and after transmission of defibrillation energy, based on patient information received from the electrodes in response to the defibrillation energy.

Wearable Defibrillator

Figure 7A:
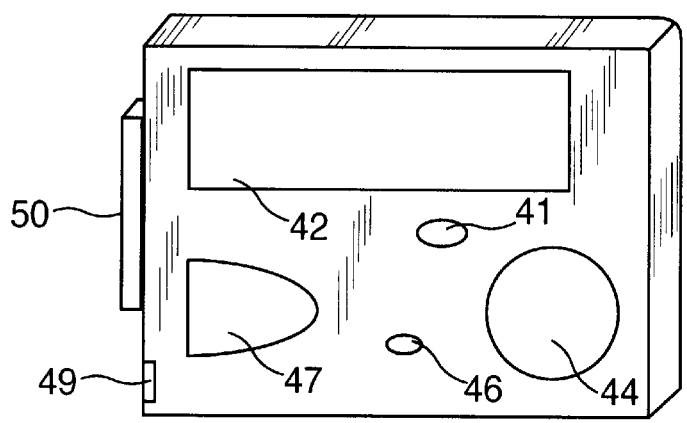
FIG. 7A shows a front view of a wearable defibrillator used in the system shown in FIGS. 1 and 2.
Figure 7B:
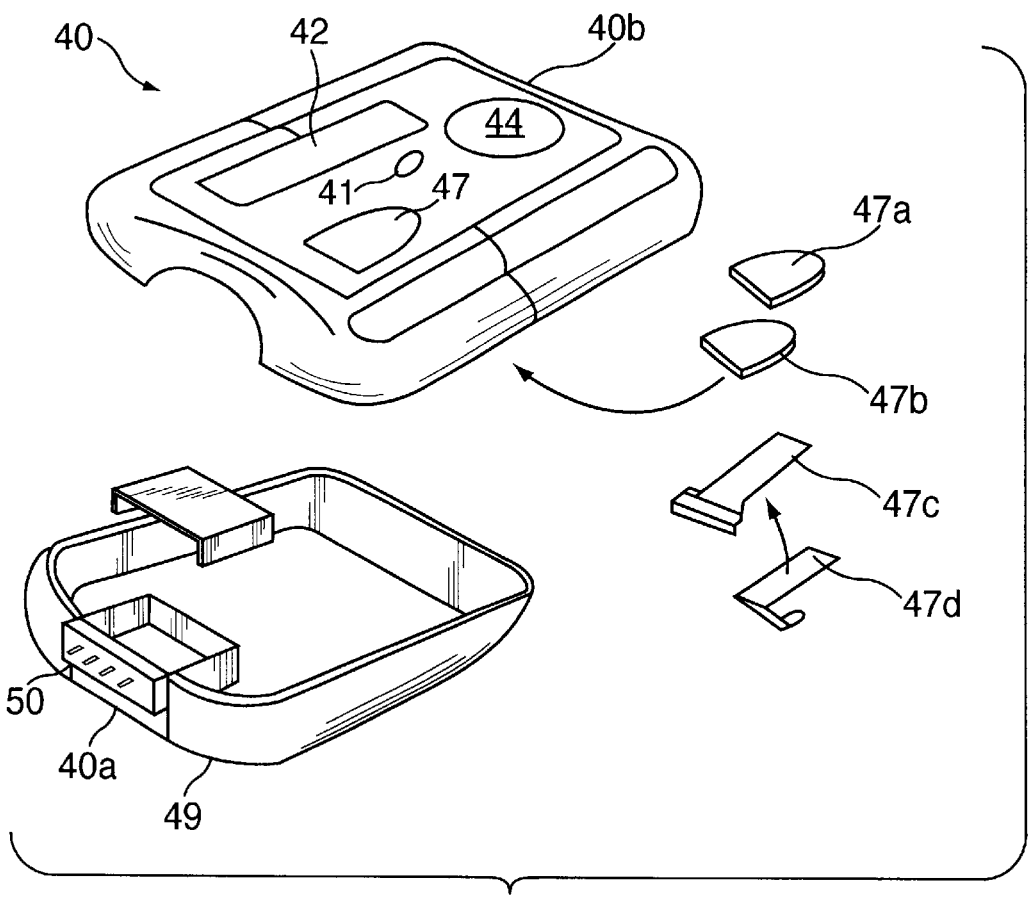
FIG. 7B is an exploded view showing the mechanical construction of the wearable defibrillator of the present invention.

A close-up view of defibrillator 10 is shown in FIG. 7A. As shown in FIG. 7A, defibrillator 10 includes housing 40, light emitting diode (hereinafter "LED") 41, visual indicator 42, auditory indicator 44, annunciator 46, user interface 47, communications link 49, and connector 50. FIG. 7B is an exploded view showing the mechanical construction of the features shown in FIG. 7A. A description of these features of the invention is provided below.

Housing 40 is preferably small enough to make the defibrillator portable, and thus wearable, yet large enough to house the circuitry included within defibrillator 10. In this regard, housing 40 can comprise a belt, or the like, which a patient can wear around his or her waist, chest, etc. However, in preferred embodiments of the invention, housing 40 comprises a rectangular casing that is roughly 6 inches in length, by 4 inches in width, by 2 inches in depth, or preferably 5.2 inches by 3.2 inches by 1.5 inches. As shown in FIG. 7B, housing 40 is comprised of base 40a and top 40b. The preferred weight of defibrillator 10 is approximately 1.5 pounds or preferably 1.0 pound or lighter. In this regard, the invention is able to achieve its small size by using high-energy capacitors (e.g., 500 $\mu$F, 400 $\mu$F, etc.) to store and deliver defibrillation energy, as described in more detail below.

Connector 50 and communications link 49 comprise external interfaces on defibrillator 10. Connector 50 is disposed on housing 40 so as to permit connection of defibrillator 10 to mating connector 21 on power supply 20 (see FIG. 2), and to permit connection of defibrillator 10 to corresponding mating connector 51 on base station 2 (see FIG. 1). To this end, connector 50 preferably includes two high-speed data pins (not shown), which permits base station 2 to interface to defibrillator 10 at a same point that electrode harness 4 interfaces to defibrillator 10. By virtue of this arrangement, information can be transmitted between defibrillator 10 and either base station 2 or a patient. Communications link 49 comprises a non-contact interface to personal computer 201 (see FIG. 2), over which information may be transmitted between defibrillator 10 and personal computer 201 (see FIG. 2) while defibrillator 10 is being worn by the patient or, if desired, at other times as well. Examples of such a non-contact interface include an infrared (hereinafter "IR") link or a radio frequency (hereinafter "RF") link.

Visual indicator 42 comprises a liquid crystal display (hereinafter "LCD") or the like (in preferred embodiments, a Standish 162SLC 2×16 dot matrix display), having two lines for displaying information, including text and errors, to a patient or to a clinician operating defibrillator 10. This information can include, but is not limited to, information concerning the patient's heart activity, such as the patient's ECG or the like; messages upon detection of abnormal activity in the patient's heart; statements indicating that the patient has been wearing electrode harness 4 for greater than a recommended period of time; instructions for the use of defibrillator 10; prompts for using defibrillator 10; errors that have occurred in defibrillator 10; messages transmitted to defibrillator 10 from an external location via base station 2, personal computer 6, or personal computer 201; an indication that one or more of sensing electrodes 31 have become detached from the patient; and an indication that defibrillator 10 cannot differentiate between artifact noise in a patient's body and a cardiac arrhythmia. In preferred embodiments of the invention, the information is displayed for about 15 seconds.

In addition to the LCD, one or more visual indicators, such as light emitting diode (hereinafter "LED") 41, may be provided on defibrillator 10 to indicate different operational states thereof. For example, in preferred embodiments of the invention, LED 41 blinks when defibrillator 10 is operating normally, is off when defibrillator 10 is without power (including when power supply 20 has failed), and is continuously illuminated during power-up error detection diagnostics performed by defibrillator 10.

Auditory indicator 44 comprises a speaker (in preferred embodiments, an MG Electronics MCS298 speaker) or the like, which provides verbal messages corresponding to information displayed on visual indicator 42. These messages may be output in a variety of different languages on both visual indicator 42 and auditory indicator 44. In preferred embodiments of the invention, auditory indicator 41 echos visual display 42, and has a volume that is adjustable at least up to 60 or 70 decibels. Auditory indicator 44 may also be configured to provide additional sounds, such as tones, buzzing, beeping, etc. to indicate error conditions within defibrillator 10. Examples of such error conditions include, but are not limited to, a low or drained power supply, improper attachment of sensing electrodes 31 to the patient, detachment of sensing electrodes 31 from the patient, and inoperability of defibrillator 10. In addition, another auditory indicator, such as annunciator 46, may also be included on defibrillator 10. Annunciator 46 is preferably separate from auditory indicator 42, and produces a buzzing or other unique sound to indicate error conditions within defibrillator 10, particularly a low or drained power supply.

User interface 47 comprises a response button, whereby a patient or clinician can provide an input to wearable defibrillator 10 simply by pressing the button. As shown in FIG. 7B, the response button is comprised silicone 47a, button 47b, paddle 47c and foil 47d. The response button cancels any upcoming defibrillation operation, meaning that, when pressed, the response button terminates a current defibrillation and, in some embodiments of the invention, disarms defibrillator 10. In preferred embodiments of the invention, the response button is relatively large, making it easily accessible to the patient, particularly through clothing and the like. In addition, in preferred embodiments of the invention, defibrillator 10 confirms when the response button has been pressed by issuing both audio and visual messages. In operation, the response button is pushed in response to, e.g., a "PLEASE RESPOND" verbal message so as to confirm patient consciousness or lack thereof. In preferred embodiments of the invention, defibrillator 10 also includes a cardiac event recording button which may or may not be separate from the response button, and which is pushed when the patient wants to record occurrence of a cardiac event. It is noted that these two functions are combined during a potential rescue situation; i.e., the patient will want to respond to the defibrillator's response requests at the same time, possibly recording the occurrence of a cardiac event. Combining these functions into a single button helps train the patient to habitually push the same button whenever there are requests from the defibrillator or cardiac events.

Figure 8:
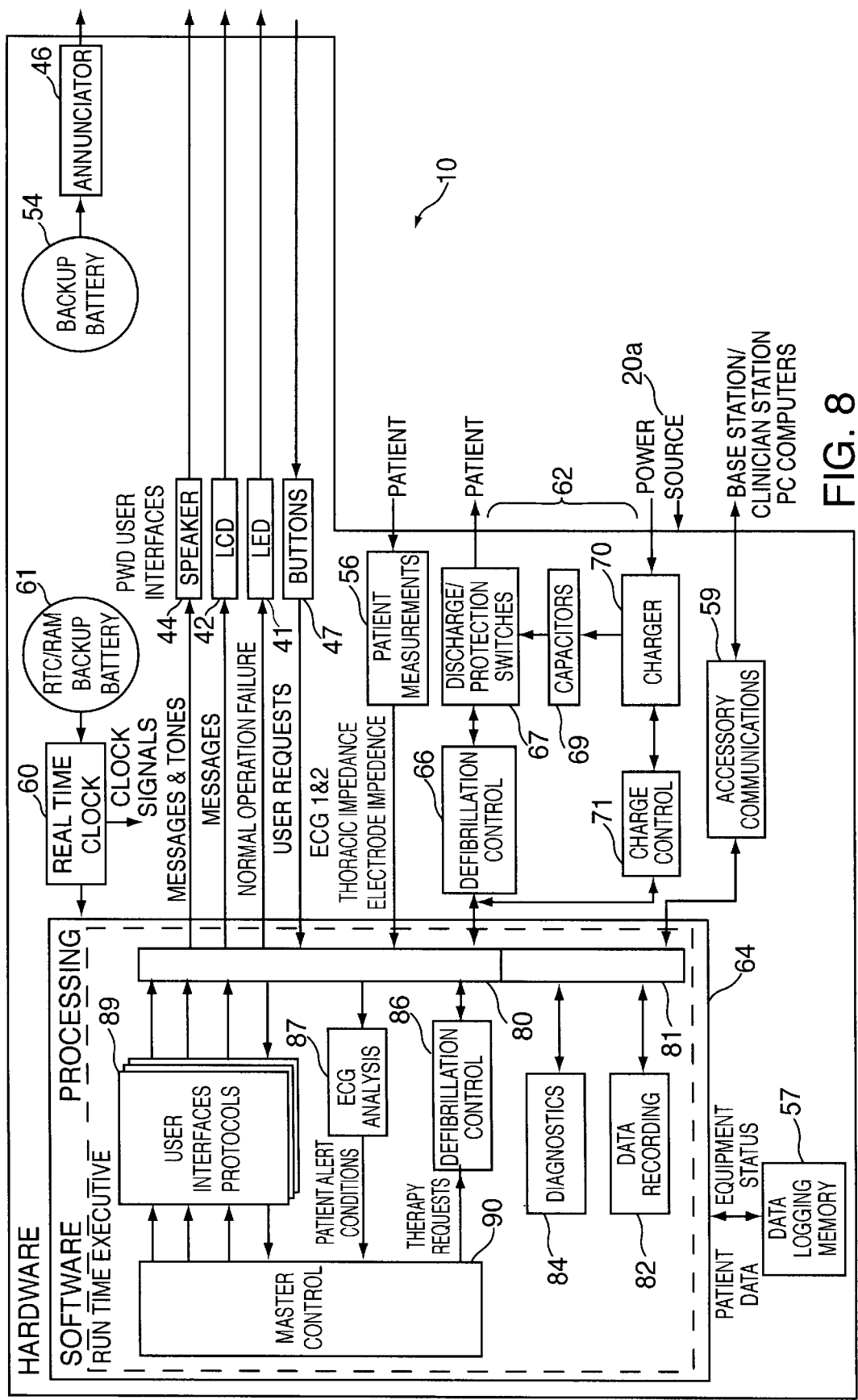
FIG. 8 shows a functional block diagram of the defibrillator shown in FIG. 7A.

FIG. 8 is a system functional block diagram of defibrillator 10. Briefly, the hardware and software functional blocks shown in FIG. 8 monitor and analyze patient information (e.g., the patient's ECG) received from electrode harness 4 in order to determine if a cardiac rhythm is life threatening and requires defibrillation, and also permits communication to base station 2, personal computer 6, and personal computer 210. In addition, these blocks within defibrillator 10 determine the patient's thoracic impedance based on information received from the patient via electrode harness 4, and adjust the defibrillation energy accordingly. Alternatively, a predetermined thoracic impedance value may be stored in data logging memory block 57. That predetermined thoracic impedance value may then be retrieved and used to adjust the defibrillation signal.

As shown in FIG. 8, defibrillator 10 comprises auditory indicator 44, visual indicator 42, LED 41, user interface 47, and annunciator 46. Descriptions of these features of the invention were provided above and, therefore, will not be repeated here. It is worth noting, however, that annunciator 46 receives power from backup battery 54, which is rechargeable, and which is independent of the primary source of power (i.e., power supply 20) for defibrillator 10. Backup battery 54 provides power to annunciator 46 in the event that power supply 20 fails, thereby giving annunciator 46 the ability to warn the patient in such an event.

Defibrillator 10 also includes patient measurements block 56, data logging memory block 57, accessory communications block 59, real time clock (hereinafter "RTC") 60, RTC/RAM backup battery 61, which may or may not be separate from backup battery 54, and signal generator 62. In the representative embodiment of the invention described herein, signal generator 62 comprises processing block 64, defibrillation control block 66, discharge/protection switches 67, capacitors 69, charger 70 and charge control block 71. In this regard, although the present invention includes the forgoing blocks in signal generator 62, any combination of hardware and/or software which effects the same function as these features can be employed in the practice of the present invention.

RTC 66 maintains the current date and time, receiving power from rechargeable RTC/RAM backup battery 61 when defibrillator 10 is powered-off. In preferred embodiments of the invention, RTC 60 is a Dallas 1306 serial RTC, which is able to maintain the correct time and date for up to 30 days without connection to power supply 20. RTC/RAM backup battery 61 also provides power to a memory (e.g., a RAM (not shown)). Accessory communications block 59 performs any filtering and protocol conversion necessary to enable transmission of data between defibrillator 10 and base station 2, personal computer 6 and/or personal computer 210. Patient measurements block 56 comprises analog signal conditioning hardware which filters and digitizes ECG signals, thoracic impedance measurements, and electrode-to-skin impedance measurements received via electrode harness 4, and which transmits the resulting data to processing block 64. Patient measurements block 56 also receives information from an accelerometer, described below, relating to the patient's motion, and provides this information to processing block 64.

Data logging memory block 57 stores both the operational history of defibrillator 10 and information relating to the patient. More specifically, data logging memory block 57 stores abnormal heart activity of the patient; the patient's ECG before, during and after application of defibrillation energy; an indication that the patient has been trained for use with defibrillator 10; analyzed ECG conditions; ECG markings, including defibrillation synch, external pace pulse, high slew rate, and saturation; patient thoracic and electrode-to-skin impedance measurements over time; voice, tone, and buzzer prompts; displayed messages; information concerning patient interaction with the defibrillator 10 (e.g., if and when the patient has pressed the response button); transmitted defibrillation waveform measurements, including current and voltage versus time; execution time measurements of defibrillator 10 for use in determining if defibrillator 10 operated as expected; detected operational errors of defibrillator 10 (including a type of error, persistence of the error, whether defibrillator 10 was in the operational mode when the error occurred, whether defibrillation had begun when the error occurred, and whether a cardiac arrhythmia had been detected when the error occurred); calibration data for defibrillator 10; the serial number of defibrillator 10; a harness identification ID of an electrode harness interfaced to defibrillator 10; cold and warm start information for defibrillator 10; artifact noise in the patient; data from an accelerometer relating to motion of the patient; documentation regarding the defibrillator; instructions on how to use the defibrillator; and patient parameters. These patient parameters include, but are not limited to, the patient's ID number which is a unique assigned identifier for each patient (range of 1 to 9,999; default=0); the patient's name; the language used for voice and corresponding text messages; a minimum audio level to which a patient responds; minimum tactile stimulation signal to which a patient responds; maximum tactile stimulation signal for a patient; pacing bradycardia rate—heartbeat rate below which bradycardia will be declared and pace rescue initiated; pace current level—current level needed to ensure pace rescue; a ventricular tachycardia rate at which defibrillation energy is to be delivered to the patient (range of 150 to 180 beats per minute (hereinafter "bpm")); the patient's thoracic impedance range, meaning, the impedance range during which defibrillation energy may be transmitted to the patient (range of 15 to 200 ohms); a time and a date at which the defibrillator was issued to the patient; a name of a clinic at an external location (e.g., central repository 9, a hospital, a doctor's office, etc.); a name of a clinician at the external location; and an electrode-to-skin impedance range which is used to determine whether the electrodes are not attached, or are improperly attached, to the patient. Also stored with the patient parameters is a checksum which is used to determine their validity.

In summary, data logging memory block essentially stores any information provided to, or transmitted from, defibrillator 10 over a predetermined span of time, such as two days. This data is preferably stored in a log format and includes time data specifying a time at which each event occurred. In addition, embedded in the data are validation and synchronization mechanisms for use in detecting areas of corrupted or missing data.

In preferred embodiments of the invention, data logging memory block 57 has a capacity (e.g., 24 megabytes or 48 megabytes) which is sufficient to record the foregoing information over a 48 hour period of continuous use of defibrillator 10. In embodiments of the invention where only a portion of the foregoing information is stored in data logging memory block 57, there may be a corresponding decrease in the size of data logging memory block 57 or a corresponding increase in the available period of use for the device. On the other hand, to achieve a reduction in the required amount of memory space without sacrificing data stored therein, it is possible to compress the data, preferably at a 4-to-1 compression ratio, and then to store the compressed data in data logging memory block 57. It is noted that the invention is not limited to compressing the data at a 4-to-1 ratio, and that any compression ratio may be used. Any of a number of well-known compression algorithms, particularly those relating to biological signal compression, may be employed to effect the necessary compression. Compression techniques that result in lossless compression, however, are preferred. In particularly preferred embodiments of the invention, data logging memory block 57 is removable, and can be transferred to the base station or to an external location at which point data stored therein may be downloaded.

Signal generator 62 generates, based on patient impedance data provided from patient measurements block 56, defibrillation energy which preferably has a bi-phasic waveform may have two phases with substantially identical durations, different durations, or a first phase with a longer duration than a second phase, and having relatively low peak amplitudes over a patient impedance range. A mono-phasic waveform or a truncated exponential waveform having similar characteristics may also be used.

FIG. 6 shows a representative example of defibrillation energy generated by signal generator 62. As shown in FIG. 6, waveform 72 has two phases 74 and 76, each of which has substantially the same durations 77 and 79 (i.e., $t_{max}$=~5.4 seconds) and a peak amplitude of less than 23 amperes (i.e., $I_{max}$=~20 A). Specifically, the bi-phasic waveform has a 5.37 msec (+/−5%) initial "positive" phase, followed by a 100 to 300 $\mu$sec zero-potential plateau (i.e., $t_{switch}$=~180 $\mu$sec), followed by another 5.37 msec (+/−5%) "negative" phase. In preferred embodiments of the invention, the amplitude at the end of the pulse is 60 to 80% of its initial value. Of course, the example shown in FIG. 6 merely representative, and waveforms having different values can also be generated by the present invention. In fact, in preferred embodiments of the invention, the duration of each phase of a bi-phasic waveform may be between 4.5 and 6.4 msec.

The waveform corresponding to the defibrillation energy preferably also has a substantially consistent tilt, as shown in FIG. 6. In preferred embodiments, the tilt of the defibrillation energy is between 53% and 79%. The present invention provides a way in which to alter this tilt using capacitors 69. In this regard, capacitors 69 store energy which is discharged to the patient via discharge/protection switches 67 in the form of the foregoing defibrillation energy. This energy is discharged as a waveform having the foregoing characteristics. The tilt of the waveform (i.e., the rate of the waveform's exponential decay) is determined by the "RC" time constant $\tau$ of the circuit used to generate the waveform. In this regard, that circuit's time constant $\tau$ may be altered by switching capacitors 69, as described below, so as to alter the overall, combined capacitance value of capacitors 69. Thus, by switching capacitors 69 in this manner, it is possible to vary the tilt of the waveform and the achieve a low-current waveform.

To ensure safe operation, the energy for defibrillation energy is discharged by capacitors 69 only in the case that a life-threatening cardiac arrhythmia is detected in the patient (as determined by comparing the patient's ECG to pre-stored patient parameters), the patient is deemed to be unconscious (as determined, e.g., by the patient's response, or lack thereof, to messages provided by auditory indicator 44, visual indicator 42, and annunciator 46), and the patient's thoracic impedance is within a predetermined range. In preferred embodiments of the invention, this range is between 15 ohms and 200 ohms. The process of determining whether and when to transmit defibrillation energy to a patient is described in more detail below. One (or more) of capacitors 69 is also used to provide the above-noted tactile stimulation signal to the patient. The tactile stimulation signal may be used to alert the patient of the occurrence of a cardiac event, and may vary based on the patient and based on which time it is administered to the patient in response to a message from the defibrillator. That same capacitor may also be used to deliver a pacing signal to the patient's heart in order to stimulate normal contractions thereof.

Figure 9:
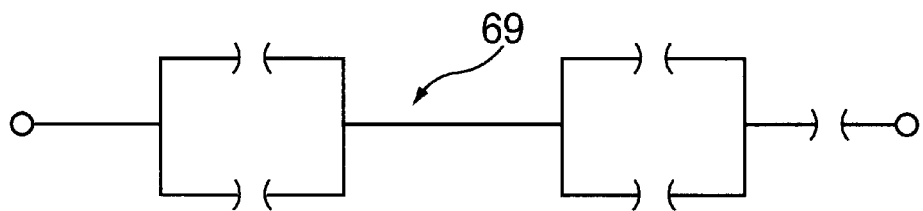
FIG. 9 shows a "221" capacitor configuration.
Figure 10:
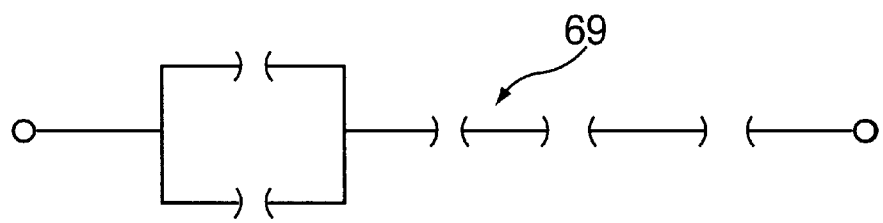
FIG. 10 shows a "2111" capacitor configuration.
Figure 11:
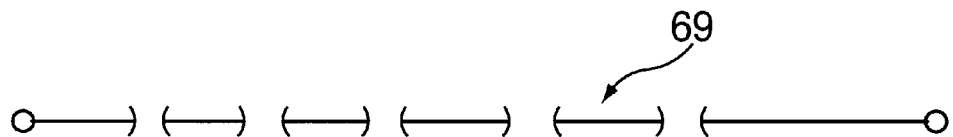
FIG. 11 shows a "11111" capacitor configuration.

The invention preferably includes 5 capacitors having capacitances of 500 $\mu$F (350 V) each; although capacitors having other capacitances may be used as well. The capacitors are switchable into the "221" configuration shown in FIG. 9, in which there are two sets of parallel capacitors in series with a single capacitor; the "2111" configuration shown in FIG. 10, in which there is one set of parallel capacitors in series with three single capacitors; and the "11111" configuration shown in FIG. 11, in which there are five single capacitors in series. In general, the higher the impedance of the patient, the lower the peak current that is required for the defibrillation energy (a lower tilt is also required at higher impedances). Consequently, the higher the impedance of the patient, the lower the capacitance that is required to generate the defibrillation energy. For example, for a patient whose impedance is relatively high (e.g., 120 ohms), the 11111 capacitor configuration may be used to generate defibrillation energy having a maximum peak current of 15 A.

In this regard, the lower the impedance of the patient, the higher the capacitance that is required to generate the defibrillation energy. Thus, for patients whose impedance is relatively low (e.g., 40 ohms), the 221 capacitor configuration may be used to generate defibrillation energy having a maximum peak current of 21 A.

Table 1, shown below, provides values for $I_{max+}$, $I_{avrg+}$, $I_{final}$, $t_{max+}$, $t_{switch}$, and $t_{max-}$ (see FIG. 6) for defibrillation energy for patients having impedances of 40, 60, 80 and 120 ohms. These values are merely representative of a particular case, and other values, of course, may be substituted therefor. In this regard, as noted above, the duration of each phase is roughly between 4.5–6.5 msec, and the peak current is roughly between 12 and 25 A.

TABLE 1

|  | 40 ohms | 60 ohms | 80 ohms | 120 ohms |
|---|---|---|---|---|
| $I_{max+}$ | 21 A | 20 A | 20 A | 15 A |
| $I_{avrg+}$ | 15 A | 15 A | 15 A | 11 A |
| $I_{final-}$ | −7.0 A | −6.0 A | −5.0 A | −5.5 A |
| $t_{max+}$ | 5.4 ms | 5.4 ms | 5.4 ms | 5.4 ms |
| $t_{switch}$ | 0.2 ms | 0.2 ms | 0.2 ms | 0.2 ms |
| $t_{max-}$ | 5.4 ms | 5.4 ms | 5.4 ms | 5.4 ms |

In addition to using capacitors 69 to control the waveform of the defibrillation energy in the foregoing manner, the invention may also include a resistor, placed in series with the capacitors. Due to the resistor's effect on the circuit's time constant, the resistor has the effect of "smoothing", i.e., decreasing the tilt of, the waveform of the defibrillation energy. In this regard, generally speaking, an increase in the resistance of the resistor decreases the tilt of the waveform. As an alternative to the foregoing configuration, the invention may include a single capacitor and one or more switchable resistors to achieve the effect of varying the circuit's time constant and thereby varying the waveform of the defibrillation energy.

As noted above, discharge/protection switches 67 control delivery of the defibrillation energy from capacitors 69 to the patient. Discharge/protection switches 67 are controlled by defibrillation control block 66 which, in turn, is controlled by processing block 64. Specifically, when defibrillator 10 is not in use, or is not required to provide an output signal, processing block 64 commands defibrillation control block 66 to open discharge/protection switches 67, thereby providing protection from unwanted electric signals. On the other hand, when processing block 64 determines that defibrillation energy is to be transmitted to the patient, processing block 64 immediately commands defibrillation block control block 66 to close discharge/protection switches 67, thereby providing the energy to the patient. In this regard, as noted above, one of capacitors 69 is also able to transmit tactile stimulation and pacing signals to the patient. In a case that a tactile stimulation or a pacing signal, as opposed to the defibrillation energy, is to be transmitted, processing block 64 issues a command to defibrillation control block 66 which, in response, may switch one of discharge protection switches 67 so as to output a signal from only one of capacitors 69. As shown in FIG. 8, defibrillator control block 66 also monitors discharge/protection switches 67 and provides the results thereof to processing block 64.

Charger 70 controls charging of capacitors 69 from power supply 20, the input of which is labeled 20a in FIG. 8. Specifically, charger 70 comprises hardware which transfers energy from power supply 20 to capacitors 69. Charger control block 71 controls charger 70 in response to commands received from processing block 64 so that capacitors 69 charge to a level commanded by processing block 64. In this regard, processing block 64 may issue commands to charge capacitors 69 to one of a plurality of different levels depending on a determined type of arrhythmia, e.g., ventricular fibrillation versus ventricular tachycardia. Thus, if a ventricular fibrillation is detected, then a signal having a higher amplitude is output, whereas if a ventricular tachycardia is detected, then a "cardio" or lower amplitude defibrillation signal is output. Processing block may also issue commands to charge processing block 69 based on a type of signal to be transmitted, e.g., defibrillation energy, a pacing impulse, or a tactile stimulation signal.

Processing block 64 can comprise a microprocessor, controller, or the like, as described below, which includes an internal program memory (not shown in FIG. 8). This memory is used to store software modules comprised of process steps that are executable by processing block 64. Specifically, process steps in these modules are executable to control operation of defibrillator 10 based on input received from a patient or, alternatively, from base station 2 (see FIG. 1). These software modules comprise input/output (hereinafter "I/O") module 80, including communications submodule 81 therein, data recording module 82, diagnostics module 84, defibrillation control module 86, ECG analysis module 87, user interface protocols 89, and master control module 90.

I/O module 80 preferably comprises a BIOS module which controls the transfer of data between software modules running within processing block 64 and hardware components within defibrillator 10. I/O module 80 also controls communications between processing block 64 and auditory indicator 44, visual indicator 42, LED 41, and user interface 47. To this end, the invention includes user interface protocols 89, between master control module 90 and I/O module 80. User interface protocols 89 comprise command sequences for controlling transmission of various prompts, such as tones, verbal messages, or the like, to the user via auditory indicator 44, visual indicator 42, and LED 41 in response to detected events, such as a cardiac arrhythmias or the like. Similarly, user interface protocols 89 include command sequences for controlling receipt of signals input by the user via user interface 47 (i.e., the response button). Communications submodule 81 controls communications between processing block 64 and an interfaced device, such as electrode harness 4 or base station 2, via accessory communications block 59. Processing block 64 also executes a low-level, run time executive (hereinafter "RTE") module (not shown), which supports communication between the various software tasks running in processing block 64.

ECG analysis module 87 comprises process steps which monitor the patient for a predetermined condition based on information provided through electrodes 31. ECG analysis module analyzes the patient's ECG and impedance data provided from sensing electrodes 31 (via patient measurements circuit 56), together with other information provided from the patient, including artifact noise and patient motion, in order to determine whether, when, and what types of arrhythmias are present in the patient's ECG.

More specifically, ECG analysis module 87 performs any necessary signal processing on the patient's ECG and thoracic impedance data in order to remove any extraneous data such as may be present due to noise in the patient's body, including artifact noise or noise caused by patient motion. Assuming that ECG analysis module 87 is able to remove extraneous noise from the patient's ECG and impedance data, ECG analysis module 87 compares the patient's ECG and thoracic impedance data to the patient parameters stored in data logging memory block 57 (e.g., the patient's thoracic impedance range and ventricular fibrillation and ventricular tachycardia rates at which defibrillation, pacing or cardio (described below) signals should be administered) in order to determine whether an arrhythmia has occurred. In the case that ECG analysis module 87 determines that an arrhythmia has occurred, ECG analysis module 87 analyzes the patient's ECG and the patient parameters in order to determine the type of arrhythmia, i.e., whether the arrhythmia comprises ventricular fibrillation, ventricular tachycardia, asystole, bradycardia, or indioventricular rhythms, and whether defibrillation energy should be transmitted to the patient in response to the arrhythmia. Specifically, ECG analysis module 87 determines if the patient's rhythm is normal, meaning that the patient has a normal heartbeat, in which case no intervention is required; bradycardia, meaning that the measured heartbeat is less than 5 bpm; ventricular fibrillation which comprises uncoordinated rapid contractions of the heart which replace normal synchronous pumping action, specifically in the heart's lower chambers; ventricular tachycardia which comprise a threatening heart condition associated with a very rapid heart rate (>150 bpm) but minimum pumping action; marginal ventricular tachycardia (between 120 and 150 bpm—referred to as "walking VTs"); noise; and non-determinate signals, which are described below. The invention may use one or more well-known analysis algorithms to make these determinations. However, in preferred embodiments of the invention, ECG analysis module 87 performs the algorithm shown in FIG. 16.

Figure 16:
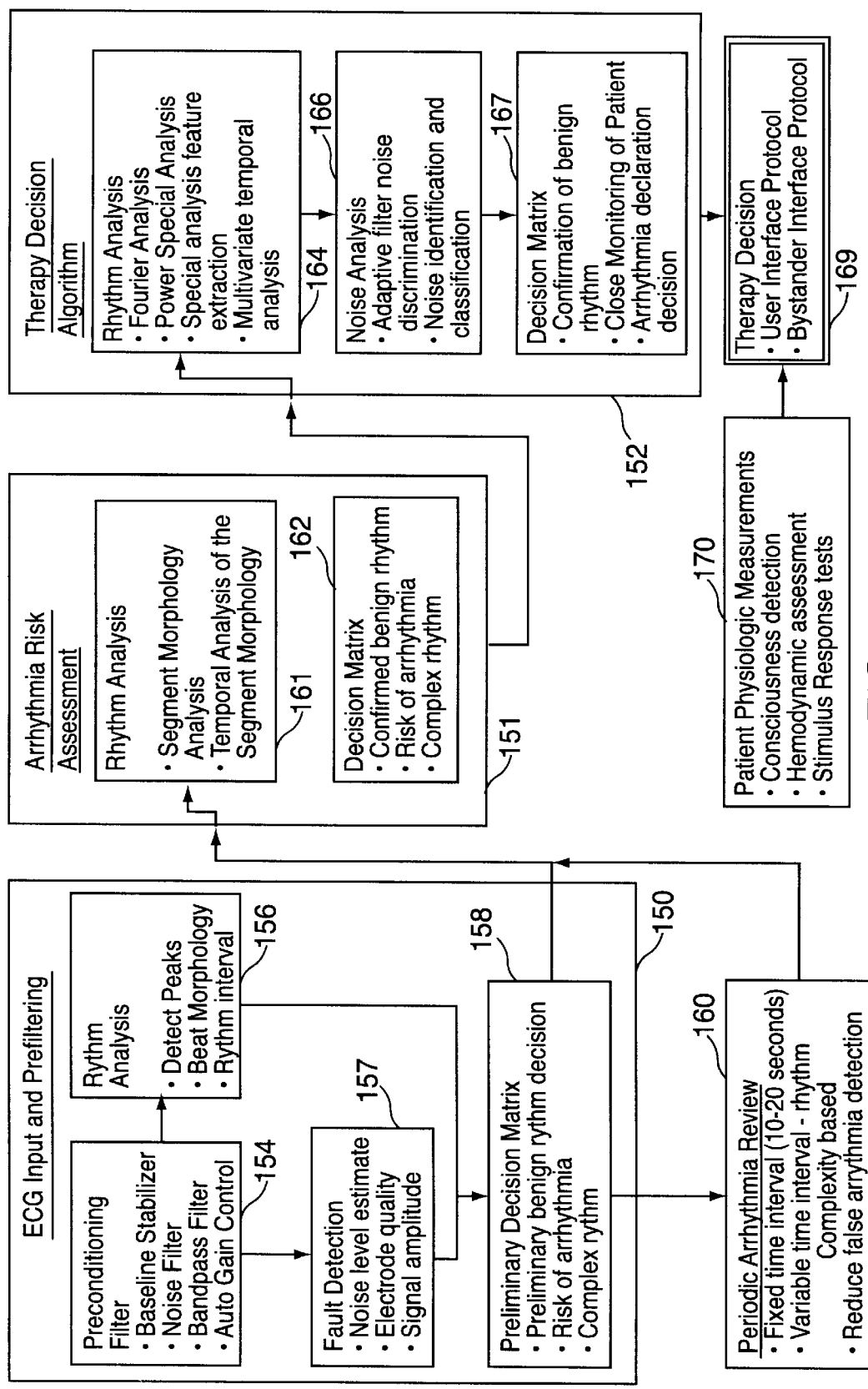
FIG. 16 is a block diagram showing a preferred algorithm used by the present invention to perform ECG analysis on received patient information.

The algorithm shown in FIG. 16 essentially includes three stages, ECG input and prefiltering stage 150, arrhythmia risk assessment stage 151, and therapy decision algorithm stage 152. ECG input and prefiltering stage 150 includes preconditioning filter step 154, during which baseline stabilizer processing, noise filtering, bandpass filtering, and auto-gain control are performed on the patient's input ECG data. In preferred embodiments, at least some of these functions are performed in hardware in patient measurements block 56 (e.g., ECG filter 119 and ECG amplifier 92 described below with respect to FIG. 13). Following preconditioning filter step 154, the ECG data is then transmitted to both rhythm analysis step 156 and fault detection step 157.

Rhythm analysis step 156 detects peaks in the patient's ECG, a beat morphology of the patient's heart, and a rhythm interval of the patient's heart. Fault detection step 157 determines a noise level estimate for noise in the patient's ECG, the electrode quality, meaning connection of electrodes 31 to the patient, and the patient's ECG signal amplitude. Results from steps 156 and 157 are provided to preliminary decision matrix 158 which makes a preliminary determination, based on the information provided from steps 156 and 157 and based on stored patient parameters, whether the patient's ECG comprises a benign rhythm, a complex rhythm, or a rhythm that constitutes a risk of arrhythmia. This preliminary determination is then provided to periodic arrhythmia review step 160. Periodic arrhythmia review step 160 samples the input ECG data for fixed time intervals (e.g., 10 to 20 seconds), or at variable time intervals for arrhythmias which are preliminarily determined to be complex. This data, along with the preliminary determination made in preliminary decision matrix 158, is then passed along to arrhythmia risk assessment stage 151, specifically to rhythm analysis step 161.

Rhythm analysis step 161 performs segment morphology analysis on data received from periodic arrhythmia review step 160, and also performs a temporal analysis of the results of the segment morphology analysis. Processing then proceeds to decision matrix 162 which either confirms or refutes the preliminary decision made in preliminary decision matrix 158 based on the processed data and stored patient parameters. Specifically, decision matrix 162 either confirms or refutes that the patient's ECG comprises a benign rhythm, an arrhythmia, or a complex rhythm. Processing then proceeds to therapy decision algorithm stage 152, specifically to rhythm analysis step 164. Rhythm analysis step 164 processes the patient's ECG data by performing thereon, a Fourier analysis, a power spectral analysis, spectral analysis extraction, and a multi-variate temporal analysis.

The processed ECG data output from rhythm analysis step 164 is then provided to noise analysis step 166. Noise analysis step 166 performs adaptive noise discrimination on the processed ECG data, and then performs noise identification and classification so as to characterize noise in the data. For example, the noise may comprise artifact nose, noise from an internal pacemaker, etc. Thereafter, processing proceeds to decision matrix 167. Decision matrix 167 either confirms that the patients ECG is a benign rhythm, in which case decision matrix 167 merely permits continued monitoring of the patient's ECG, or declares that there is an arrhythmia. The results of decision matrix 167 are then output to therapy decision step 169, which determines whether to provide defibrillation energy to the patient based on the results of decision matrix 167, together with patient physiologic measurements provided by step 170. These physiologic measurements include consciousness detection, hemodynamic assessment, and stimulus response tests.

By virtue of the foregoing, ECG analysis module 87 is able to differentiate "treatable rhythms", meaning ECG and physiologic analysis results which warrant application of therapy, from "non-treatable rhythms", meaning ECG and physiologic analysis results which do not warrant application of therapy. Non-treatable rhythms include normal sinus rhythms, supraventricular tachycardia, atrial fibrillation (with or without bundle branch block), atrial flutter, second and third degree heart block, ventricular ectopy, premature ventricular contractions, and pacing (see below). ECG analysis module 87 is also capable of recognizing spontaneous organized cardiac rhythms that frequently follow defibrillation, and are associated with the presence of pulse and blood pressure. These rhythms are also classified as non-treatable. Treatable rhythms include ventricular fibrillation (coarse), and high rate ventricular tachycardia that are hemodynamically compromised and result in patient unconsciousness. For ventricular fibrillation, the peak-to-peak amplitude should be greater than 150 $\mu V$ for the rhythm to be considered treatable, and for a ventricular tachycardia the patient's rate must exceed the corresponding patient parameter, namely the patient parameter corresponding to the ventricular tachycardia rate at which defibrillation energy (or a cardio signal (i.e., a low-energy defibrillation signal)) is to be delivered to the patient.

When identifying treatable versus non-treatable rhythms, the foregoing process errs on the side of caution, meaning that it is more likely that the ECG analysis module 87 will identify a non-treatable rhythm as treatable, than identify a treatable rhythm as non-treatable. This feature is built into the system as a safety measure, so that the likelihood of misidentifying a life-threatening arrhythmia is reduced.

ECG analysis module 87 is also able to identify other rhythms. These include non-determinative rhythms and pace rhythms. Pace rhythms correspond to heart rates that are sustained below 30 bpm and which result in patient unconsciousness. These rhythms are treated with a pacing signal, as opposed to a full defibrillation/cardio signal. Non-determinate rhythms comprise rhythms which require additional analysis to make a definitive decision as to whether defibrillation is required in response thereto. Such rhythms may be the result of extraneous artifact noise in the patient's body caused, e.g., by muscle contractions resulting from movement. In the event that ECG analysis module 87 is unable to differentiate between extraneous noise and the patient's ECG, ECG analysis module 87 notifies master control module 90 which, in turn, outputs a message to visual indicator 42 and/or auditory indicator 44.

In addition to the foregoing, ECG analysis module 87 is able to determine, based on electrode-to-skin impedance data received from electrodes 31 and the electrode-to-skin impedance range stored in data logging memory block 57, whether and which electrode in electrode harness 4 has become detached from the patient. To this end, patient measurements block 56 preferably monitors separate, identifiable terminals which permits ECG analysis module 87 to identify inputs from particular electrodes in electrode harness 4. In the case that one or more of these electrodes has become detached from the patient, ECG analysis module 87 passes such information along to master control module 90. ECG analysis module 87 is also able to determine whether electrodes are attached to the patient's skin based on thoracic impedance measurements. That is, if the patient thoracic impedance is determined to be above a predetermined value, such as 200 ohms, ECG module ascertains that the electrodes are no longer attached to the patient.

ECG analysis module 87 also determines the patient's heart rate and "R-wave synchronization trigger" based on received ECG information. In this regard, R-waves are present in the patient's ECG, both intrinsically and, in some cases, due to an internal or external pacemaker. Transmission of defibrillation signal (in this case a cardio signal) to the patient must be synchronized with an R-wave in order to avoid triggering ventricular fibrillation during a vulnerable period of the patient's ventricles. This vulnerable period occurs during repolarization of the ventricles, and usually begins 30 to 40 msec before the apex of a T-wave in the patient's ECG, and ends near the apex of the T-wave. If ventricular ischemia is present, the vulnerable period starts approximately at the same time, but may persist for as long as 120 msec after the end of the T-wave. In all cases, however, the onset of the vulnerable period follows the peak of the R-wave by an amount of time that depends on the patient's heart rate and on the patient's ECG. The onset ranges from approximately 220 msec at a heart rate of 60 bpm to 120 msec and to as low as 100 msec at a heart rate of 150 bpm. The R-wave synchronization trigger determined by ECG analysis module 87 is used by master control module 90, described below, to synchronize the defibrillation energy so that the defibrillation energy is not applied during these vulnerable periods. Specifically, defibrillation energy is synchronized so that it is delivered within 60 msec of the patient's R-wave peak, if one is present. If no R-wave is detected within a 500 msec monitoring window, then the defibrillation energy is transmitted at the end of this window. In determining the R-wave synchronization trigger, ECG analysis module 87 disregards stand-alone pacemaker pulses, meaning that only the heart's reaction to these pulses is factored into determination of the R-wave synchronization trigger, and not the pacemaker pulses themselves.

Figure 12:
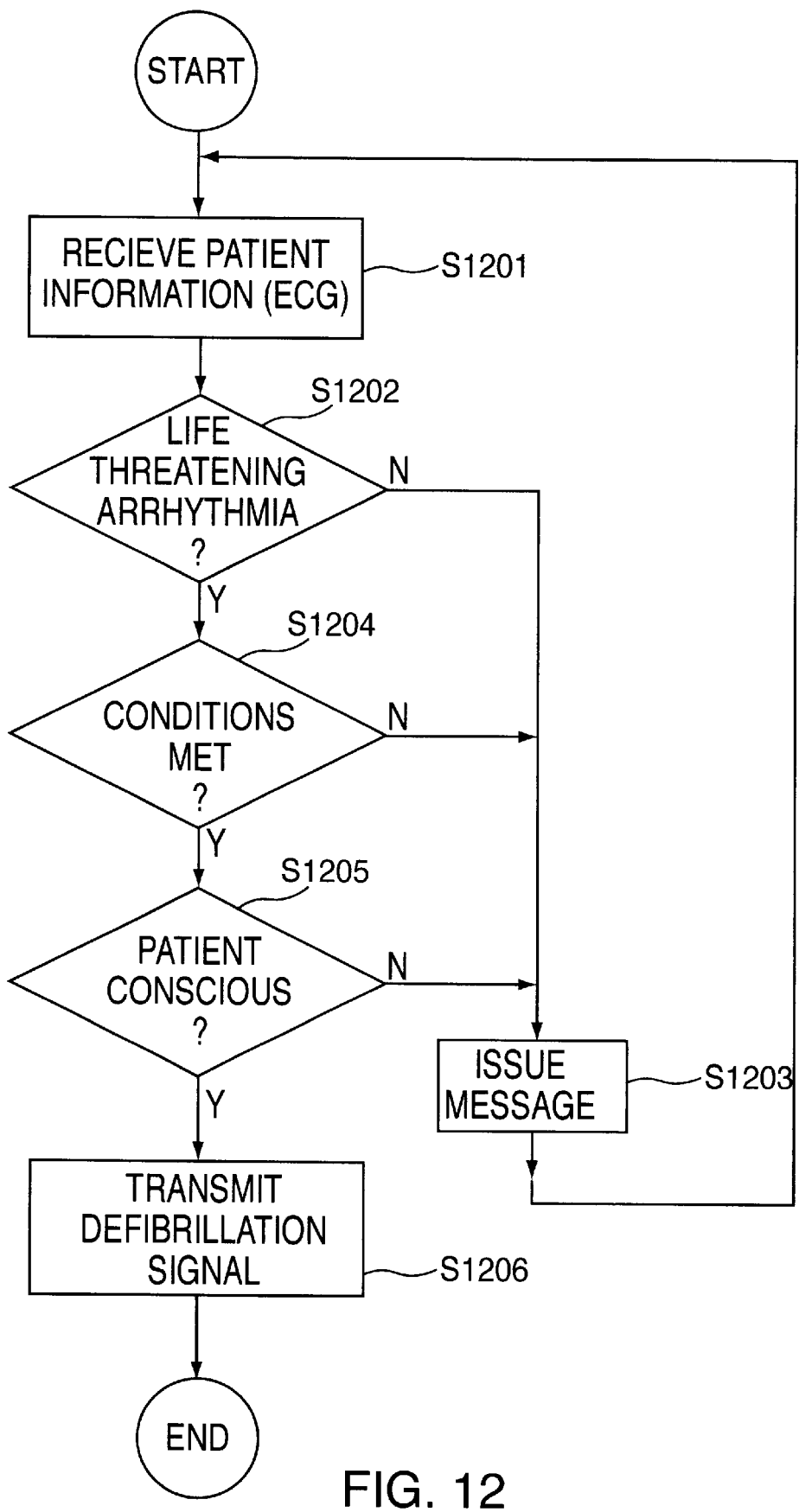
FIG. 12 is a flow diagram depicting general operation of the wearable defibrillator of FIG. 7A.

Master control module 90 integrates patient information from ECG analysis module 87, patient responsiveness from user interface 47, and outputs to auditory indicator 44, visual indicator 42, and LED 41. FIG. 12 is a flow diagram which provides an overview of this aspect of master control module 90's operation, including some operational aspects of ECG analysis module 87. In step S1201 of the flow diagram, master control module 90 receives analysis results from ECG analysis module 87, which indicate whether the patient has suffered an arrhythmia, the type of arrhythmia that the patient has suffered, and whether the arrhythmia is life threatening. Master control module 90 also receives information concerning the patient's thoracic impedance. As described below, this information is used to determine the amplitude of the defibrillation energy to be transmitted by defibrillator 10.

After step S1201 receives the ECG analysis results and impedance information, processing proceeds to step S1202, which determines whether the analysis results indicate that the patient has suffered a life-threatening arrhythmia. In a case that step S1202 determines that the patient has not suffered a life-threatening arrhythmia, processing proceeds to step S1203. Step S1203 issues commands to output a message, such as "SEE A DOCTOR", to the patient, in the form of audio and visual signals via audio indicator 44 and visual indicator 42, respectively. Thereafter, processing returns to step S1201.

On the other hand, in the case that step S1202 determines that the patient has suffered a life-threatening arrhythmia, processing proceeds to step S1204. Step S1204 determines whether other pre-conditions have been met before defibrillation energy is transmitted to the patient. Specifically, step S1204 determines whether the patient's thoracic impedance is within a predetermined range, preferably between 15 and 200 ohms, and whether the patient's ECG has been confirmed by, e.g., both ECG 1 and ECG 2 above taking into account artifact noise in the patient's body. In a case that step S1204 determines that these pre-conditions have been met, processing proceeds to step S1205; otherwise processing proceeds to steps S1203 and back to step S1201.

Step S1205 determines whether the patient is conscious. More specifically, in step S1205, master control module 90 outputs a message (e.g., a query) such as "ARE YOU THERE". This message is output both visually and audibly. After the message is output, master control module 90 waits a predetermined period of time for a response signal. This response signal may be input by the patient via user interface 47, specifically, by pressing the response button. In a case that master control module 90 detects the response signal within the predetermined period of time, master control module 90 ascertains that the patient is conscious. Since defibrillator 10 does not administer defibrillation energy to conscious patients, in this case, master control module 90 will not cause defibrillation energy to be transmitted to the patient. Instead, processing proceeds to step S1203, in which master control module simply issues instructions to the patient, which can vary depending upon the severity of the arrhythmia.

Thus, by pressing the response button, transmission of defibrillation energy to the patient is averted. In this regard, transmission of the defibrillation energy can also be averted upon detection of certain errors in the defibrillator, disconnection of electrode harness 4 from defibrillator 10, and removal of sensing electrodes 31 from the patient.

In step S1205, in a case that master control module 90 does not detect a response signal within the predetermined period of time, master control module 90 issues another audio or visual message (e.g., a louder message). After this second message has been transmitted to the patient, master control module 90 again waits for a response from the patient. In a case that the patient does not respond to this second message within a predetermined period of time, master control module 90 issues a third message to the patient. This message can be a still louder message or can include a tactile stimulation signal which is transmitted via an electrode on the patient. If the patient does not yet respond, master control module 90 issues a fourth and final message together with a tactile stimulation signal. In this regard, it is noted that the format of these four messages can vary. For example, verbal messages need not be louder, the tactile stimulation signal can increase in intensity with each message or may be applied at each message, etc. Moreover, there need not be four messages. Rather, there can be more or less messages, as desired.

In the event that the patient responds to none of the foregoing messages, master control module 90 ascertains that the patient is unconscious. In this case, processing proceeds to step S1206, in which case master control module 90 immediately thereafter issues a command to defibrillation control module 86 instructing that the defibrillation energy be transmitted to the patient. That is, in preferred embodiments of the invention, as soon as the patient is determined to be unconscious, master control module causes defibrillation energy to be transmitted to the patient immediately, without waiting for further input from the patient, a clinician, or other party. Included with the command to transmit the defibrillation energy is data defining the amplitude and duration of phases in the defibrillation energy. Master control module 90 determines this information based on the measured thoracic impedance of the patient (see, e.g., Table 1 above).

In preferred embodiments of the invention, the defibrillator trains patients with periodical tests in use of the response button via a response test training protocol. Clinicians introducing the defibrillator to new patients are able to initiate execution of the protocol from an attached clinician station (not shown). The same protocols that are be used to periodically test (and train) patients whenever the electrodes are replaced. The protocol is based on first two alert levels (described below) and an imminent response protocol (i.e., when the patient must response to a message from the defibrillator) so that the patient learns and becomes familiar with the first part of the imminent response protocol. The patient learns what the voice message prompt sounds like at Level 1, and learn what the Level 2 combined voice and tactile simulation signal sounds and feels like. The repetition of the Level 2 prompts is to ensure that the patient was given more than enough time to response. The response/test training protocol serves to develop a habitual reaction in the patient to the push response button in response to voice and tactile stimulation signal prompts during a potential rescue situation; regularly expose the patient to the "PLEASE RESPOND" voice menage prompt at Level 1, Level 2 with tactile stimulation signal if they do not respond to the first prompt; indirectly show the patient that before electrical therapy will be applied to them, they will be exposed to a series of voice and tactile stimulation signals to confirm that the patient is unconscious each time the test is performed, establish that the defibrillator is generating the voice and tactile stimulation prompts and that the patient can hear/feel them, can respond, and the defibrillator is registering the response; each time, record how fast the patient is responding to the prompts; and each time, determine that patient interface is working and, otherwise, declare the defibrillator unusable.

In some embodiments of the invention, in a case that a patient is determined to be unconscious, master control module 90 may also cause a message, such as "STAND BACK", to be output prior to defibrillation so as to advise bystanders of an upcoming defibrillation. In this regard, other messages may be provided to bystanders as well. For example, it is possible to output a message such as "CALL FOR HELP" in the event that a patient wearing the defibrillator is unconscious. Such a message may even be output after defibrillation energy is administered to the patient. In this regard, any number of different types of messages may be included in the invention, which may be output at any time during the defibrillation process.

In addition to applying defibrillation energy to the patient, master control module 90 also determines when it is time to provide a pacing signal to the patient, and applies that signal accordingly. This process is similar to the above process for applying defibrillation energy. That is, in a case that master control module 90 determines that a patient's heart rate is below 30 bpm and the patient is unconscious, a pacing signal may be applied via the electrode harness 4.

Defibrillation control module 86 controls defibrillation control block 66 and charge control block 71 in accordance with the command received from master control module 90 so that defibrillation energy which is appropriate for the patient can be generated and transmitted to the patient.

Regarding the remaining software modules executing within processing block 64, diagnostics module 84 performs diagnostics on defibrillator 10 relating to the operation and safety thereof prior to transmitting defibrillation energy to the patient. These diagnostics include diagnostics that are performed at power-on of defibrillator 10 in order to determine if there are operational defects therein. In a case that diagnostics module 84 detects operational defects as a result of these diagnostics, this information is stored in data logging memory block 57 and is transmitted back to master control module 90, which alerts the patient. Such information also may be transmitted to base station 2 or to personal computer 6.

Data recording module 82 controls transmission of data between defibrillator 10, base station 2 and computers 6 and 210. This data can include as noted above, abnormal heart activity of the patient; the patient's ECG before, during and after application of defibrillation energy; analyzed ECG conditions; ECG markings, including defibrillation synch, external pace pulse, high slew rate, and saturation; patient thoracic and electrode-to-skin impedance measurements over time; voice, tone, and buzzer prompts; displayed messages; information concerning patient interaction with the defibrillator 10; transmitted defibrillation waveform measurements, including current and voltage versus time; execution time measurements of defibrillator 10 for use in determining if defibrillator 10 operated as expected; detected operational errors of defibrillator 10; calibration data for defibrillator 10; the serial number of defibrillator 10; a harness identification ID of an electrode harness interfaced to defibrillator 10; cold and warm start information for defibrillator 10; artifact noise in the patient; data from an accelerometer relating to motion of the patient; and patient parameters. Data recording module 82 also controls storage of the foregoing data in data logging memory block 57.

Figure 13:
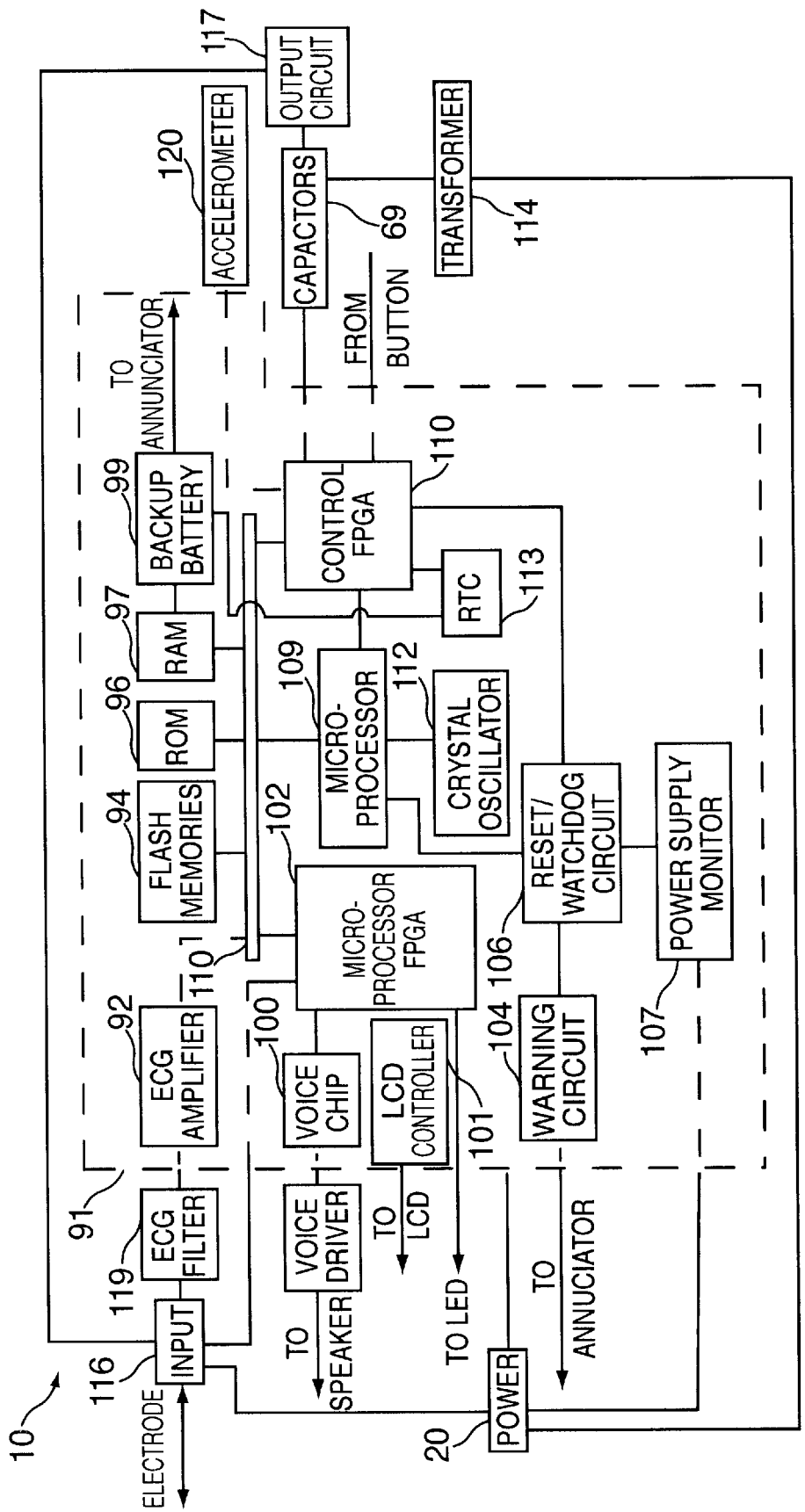
FIG. 13 is a block diagram of electrical circuitry used in the preferred embodiment of the present invention to implement the functions shown in FIG. 8.

FIG. 13 is a block diagram showing representative hardware used to implement the functions of defibrillator 10 described above with respect to the FIG. 8. The hardware components shown in FIG. 13 include processor board 91, which is comprised of ECG amplifier 92, flash memories 94, program ROM 96, static RAM (hereinafter "SRAM") 97, backup battery 99, voice chip 100, LCD circuit 101, processor field programmable gate array (hereinafter "FPGA") 102, voice driver 103, output circuit 104, reset/watchdog circuit 106, power supply monitor 107, microprocessor 109, control FPGA 110, address and data bus 111, crystal oscillator 112, and RTC 113. Also included within defibrillator 10 are capacitors 69, transformer 114, power supply 20, input circuitry 116, output circuitry 117, ECG filter 119, and accelerometer 120.

Generally speaking, processor 109, processor FPGA 102 and control FPGA 110 perform the functions of processing block 64; flash memories 94 perform the functions of data logging memory block 57; control FPGA 110 performs the functions of defibrillation control block 66, charge control block 71, and charger 70; processor FPGA 102, input circuitry 116, ECG filters 119, accelerometer 120, and ECG amplifiers 92 perform the functions of patient measurements block 56; and control FPGA 110, together with a serial interface (not shown) and a non contact interface (not shown), perform the functions of accessory communications block 59. Remaining hardware components of FIG. 13 that perform the functions shown in FIG. 8 are self-evident.

The hardware components shown in FIG. 13 are all tied to an internal, "floating" ground during operation of defibrillator 10. This means that there are no connections to an external ground when defibrillator 10 is interfaced to a patient (although there may be external ground connections when defibrillator 10 is interfaced to base station 2). The use of floating grounds during operation of defibrillator 10 is important from the patient's perspective, since it reduces the chances of unwanted electric shock to the patient. This floating ground may be on power supply 20, which was described above. A detailed description of power supply 20 is therefore omitted here for the sake of brevity. Suffice it to say that power supply 20 provides power to all components on defibrillator 10, including processor board 91, input circuitry 116, and capacitors 69.

Accelerometer 120 measures a patient's motion and provides this information to processor 109 via control FPGA 110. Processor 109 analyzes the information received from accelerometer 120, stores information relating to patient motion, and uses this information in its calculations of artifact noise noted above.

Input circuitry 116 receives signals from each of sensing electrodes 31, negative and positive inputs from power supply 20, and a connector ID from an interfaced device. Input circuitry 116 also controls output of defibrillation, tactile stimulation and pacing signals to a patient. To this end, included within input circuitry 116 are a plurality of switches, one corresponding to each input/output. These switches open and close in response to instructions from processor board 91 so as to ensure that signals, such as the defibrillation energy, are not inadvertently transmitted to a patient. Input circuitry 116 also includes shielding and the like on its input/output signal lines so as to reduce the chances of damage to defibrillation circuitry during application of defibrillation energy to the patient.

Signals received from input circuitry 116 are transmitted to ECG filter 119. ECG filter 119 comprises plurality of bandpass filters used to filter signals received from electrode harness 4. These filtered signals are transmitted to ECG amplifier 92 on processor board 91. ECG amplifier 92 includes amplifying circuitry for amplifying the filtered signals received from ECG filter 119, and an analog-to-digital converter for converting the amplified signals from analog form into digital form. These digital signals are then transmitted to processor 109 via processor FPGA 102.

Processor 109 receives clocking signals from crystal oscillator 112, which preferably provides signals up to 40 MHz. Processor 109 can comprise a microprocessor, microcontroller, or the like, and is used to execute the software modules described above so as to control operation of defibrillator 10. Examples of microprocessors which have been identified as suitable for use with the present invention include the Intel 196 processor family, Intel 386EX (386EXTB), TMS320F206, Motorola 68332, the TI "2×3" family DSP Processor, Amtel 8051 or equivalent, Hitachi 8/500 series, Mitsubishi M37700, and Motorola 68HC16, to name a few. Processor 109 also controls the application of power to other components in defibrillator 10, particularly those on processor board 91, and is able to cause these components to be powered-up and powered-down for predetermined time intervals. This feature of the invention reduces the amount of power consumed by defibrillator 10.

As another power saving feature, processor 109 is capable of operating in different modes, during which processor 109 consumes different amounts of power. Specifically, processor 109 is operable in a normal mode, during which processor 109 samples data from electrodes 31 and controls defibrillator 10 in the manner described herein. Processor 109 is also operable in a low-power mode. In some embodiments of the invention, processor 109 may be turned off completely. In preferred embodiments, however, most processing in processor 109 ceases, but some elementary routines remain running. During the low-power mode, all internal registers in processor 109 retain their data, thereby making it possible for processor 109 to resume normal operation upon re-entering the normal mode. Processor 109 enters the low-power mode periodically, e.g., at intervals of 1 to 2 ms, for predetermined periods of time, e.g., 20 ms. Alternatively, processor 109 can operate in the low-power and normal modes at equal intervals, such as every 4 ms.

In preferred embodiments of the invention, the length of time that processor 109 operates in the low-power mode is variable based on information received from the patient or, alternatively, based on information received from central repository 9. For example, if processor 109 determines based, e.g., on the patient's ECG and previous history, that the patient is at a relatively low risk for a cardiac arrhythmia, processor 109 can lengthen the period of the low-power mode. Likewise, if processor 109 determines, based on similar information, that the patient is at a high risk for an arrhythmia, processor 109 can shorten, or even eliminate, the low-power mode.

Another feature of the low power mode is that the amount of power consumed therein may be varied. For example, in a case that processor 109 determines that benign rhythms have occurred for a relatively long time, processor 109 may enter a "deep" low power mode, in which processor 109 is off, or in which only the most elementary of routines remain running. On the other hand, in a case that processor 109 determines that a treatable rhythm occurred recently, processor 109 may enter a "light" low power mode, in which less power is consumed than when the processor operates in the normal mode, but in which more than just elementary routines remain running in the processor.

To enter the low-power mode, in preferred embodiments of the invention, processor 109 simply executes an "IDLE" instruction, during which most internal processing in processor 109 is disabled. In response to this IDLE instruction, processor 109 stops its internal clock and may execute only low-level routines so as to perform minimal tasks, such as determining when it is time to re-enter the normal mode. To this end, in the low-power mode, processor 109, via control FPGA 110 (described below), monitors signals received from RTC 113 and, based on these signals, determines when it is time to re-enter the normal mode. In a case that defibrillator 10 includes a button or the like (not shown) on its user interface for placing processor 109 in the normal mode manually, processor 109 also monitors such a button during the low-power mode.

Flash memories 94 comprise removable EPROMs or the like. Program ROM 96 stores the software modules described above with respect to FIG. 8 which are executed by processor 109. Static RAM 97 comprises a memory out of which those software modules may be executed. As described above, SRAM 97 is backed-up by backup battery 99. In this regard, backup battery 99 contains a rechargeable lithium coin cell battery which is sufficient to back up both RTC 113 and SRAM 97. Battery backup 99 may also be used to supply power to power annunciator 46. Alternatively, a second backup battery (not shown) may be used for this purpose.

Reset/watchdog circuit 106 monitors processor 109 and control FPGA 110 in order to determine if either processor 109 or control FPGA has lost program control. For example, in a preferred embodiment of the invention, control FPGA 110 outputs a square wave signal called WATCHDOG_OUT in a case that control FPGA 110 and processor 109 are communicating properly. Reset/watchdog circuit 106 monitors this signal for variations therein. In a case that this signal is interrupted, or has an unexpected waveform, reset/watchdog circuit 106 ascertains that there has been a system malfunction. As another example, processor 109 is programmed to generate a signal called CONTROL_PLD_FAULT in a case that control FPGA 110 has failed. Reset/watchdog circuit 106 monitors for this signal as well in order to ascertain if there has been a failure in control FPGA 110.

In the event that either processor 109 or control FPGA 110 has failed, a system reset will be attempted by reset/watchdog circuit 106. If the problem persists, reset/watchdog circuit 106 will instruct output circuit 109 to output an alarm, e.g., a "tone" or a "buzzing" via annunciator 46. In this regard, in the event of a system error which causes a reset to be asserted, an alarm will not be sounded immediately. That is, if the system successfully recovers after one reset, no alarm will be sounded. This design allows the system to rebound from a temporary fault without alerting the user unnecessarily. If, however, a persistent fault condition exists which reasserts itself for at least 200 msec per second, the alarm is sounded for 5 to 10 seconds. If the system subsequently recovers, the alarm will cease to sound at the conclusion of this 5 to 10 second period; otherwise, the alarm will continue as long as the system reset signal is asserted for 200 msec or more per second, stopping only when the backup battery for annunciator 46 has been drained.

The system will also reset itself if power output by power supply 20 drops below a predetermined level or goes above a predetermined level. To determine if power supply 20 has gone below or above these predetermined levels, power supply monitor 107 monitors power supply 20. In preferred embodiments of the invention, power supply monitor comprises plural comparators with associated circuitry for making these determinations. In a case that power supply 20 is low, or is outputting greater than a predetermined amount of power, this information is transmitted to reset/watchdog circuit 106. In response, reset/watchdog circuit 106 causes annunciator 46 to output an alarm via output circuit 104. In a case that power supply 20 has failed, processor 109 shuts down defibrillator 10 just after reset/watchdog circuit 106 has caused annunciator 46 to output the alarm.

Processor board 91 also includes control FPGA 110 and processor FPGA 102, which comprise glue logic for controlling inputs to, and outputs from, processor board 91. Processor FPGA 102 contains memory page registers, glue logic, and processor internal clock stopping/starting circuitry. This clock stopping/starting circuitry stops an internal clock of processor 109 for predetermined periods of time, such as 4 msec, during processor 109's low-power modes. Processor FPGA 102 also controls outputs to LED 41, auditory indicator 44 and visual indicator 42 (see FIG. 8). In this regard, interfaced to processor FPGA 102 is voice chip 100, e.g., an ISD33000 series Chip Voice Record/Playback device which can store up to 60 seconds of prerecorded voice messages. Voice driver 103 is also required to drive auditory indicator 44. An example of such a driver is a TI TPA4861D (SOIC-8). Defibrillator 10 also includes LCD controller/driver 101 which, in preferred embodiments of the invention, is an OKI MSM6555B or MSM6665 chip.

Control FPGA 110 contains a defibrillator state machine and various registers for controlling operations of defibrillator 10. Among these registers are capacitor configuration registers (not shown). By writing into these registers, capacitors 69 can be programmed to enable different capacitor configurations, i.e., the 221, 2111 or 11111 configurations shown in FIGS. 9 to 11. More specifically, control FPGA 110 includes CAP_SW1, CAP_SW2, CHRGELCB and CHARGE registers. Writing a "1" into the CHARGE register enables capacitor charging, whereas writing a "0" into the CHARGE register disables charging. Writing a "1" into the CHRGELCB register switches all capacitors into a parallel configuration for charging, whereas writing a "0" into the CHRGELCB register charges only one of capacitors 60 and allows that one of capacitors 69 to be placed into a series configuration for transmitting a tactile stimulation or pacing signal. Writing a "1" into the CAP_SW1 register switches two of capacitors 69 into a series configuration, whereas writing a "0" into CAP_SW1 register switches the two of capacitors 69 into a parallel configuration. Writing a "1" into the CAP_SW2 register switches two others of capacitors 69 into a series configuration, whereas writing a "0" into CAP_SW2 register switches the two others of capacitors 69 into a parallel configuration. Thus, values in CAP_SW1 and CAP_SW2 control the configuration of capacitors 69 during a defibrillation.

Control FPGA 110 comprises a plurality of other registers as well, including a defibrillator control register. Bits are written to the defibrillator control register to set defibrillator 10 to provide either defibrillation energy, a tactile stimulation signal, or a pacing signal. Control FPGA 110 also has a number of other functions, including monitoring the charge in capacitors 69 and adjusting the charge based on signals (e.g., patient impedance) received from an interfaced device such as electrode harness 4, monitoring inputs from user interface 47, e.g., the response button, and providing output via a serial interface (not shown) to base station 2 and via a non-contact interface (not shown) to personal computer 6.

Figures 14, 14A:
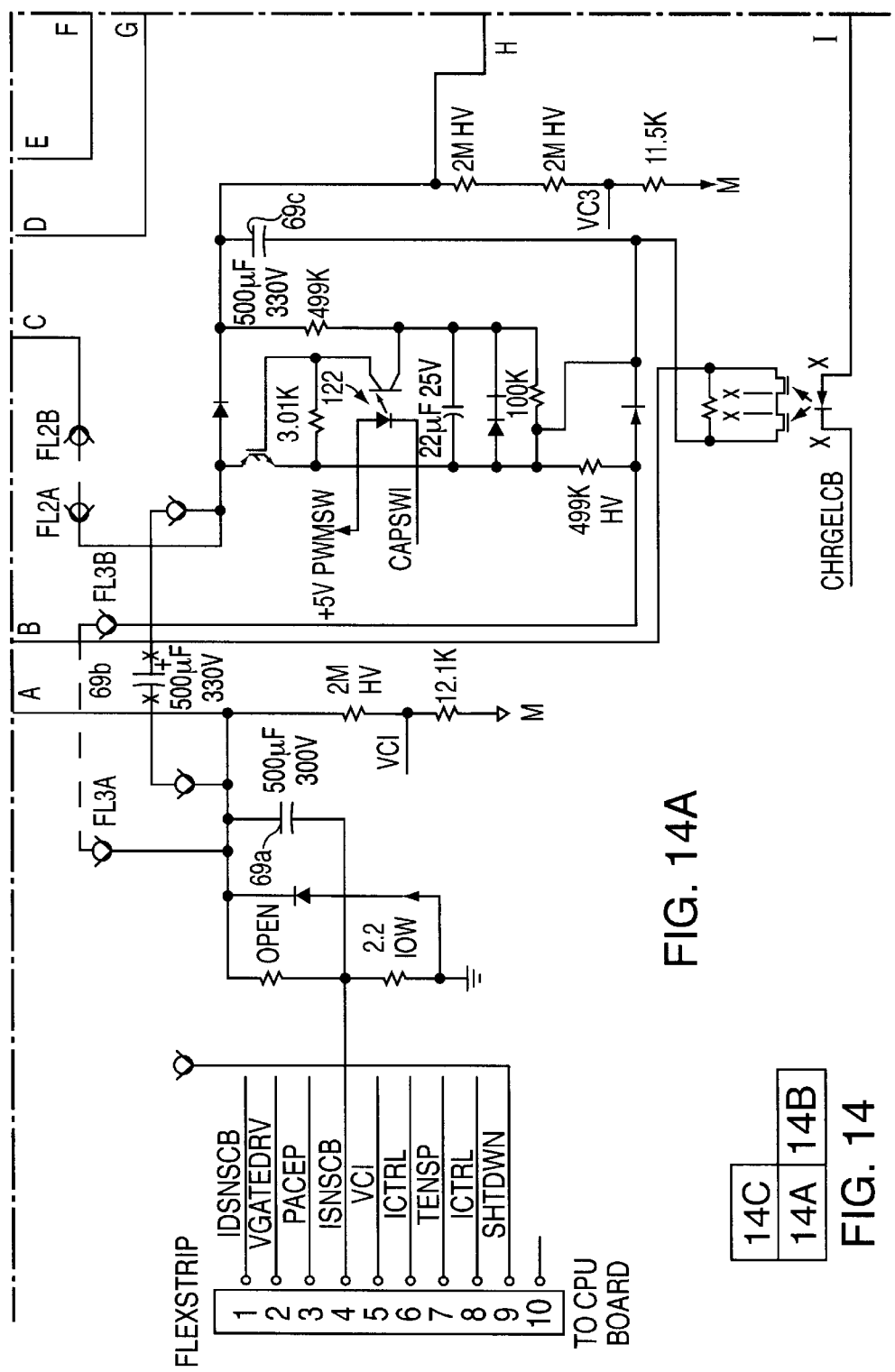
FIGS. 14A–14C show details of a capacitor switching circuitry in the preferred embodiment of the present invention.
Figure 14B:
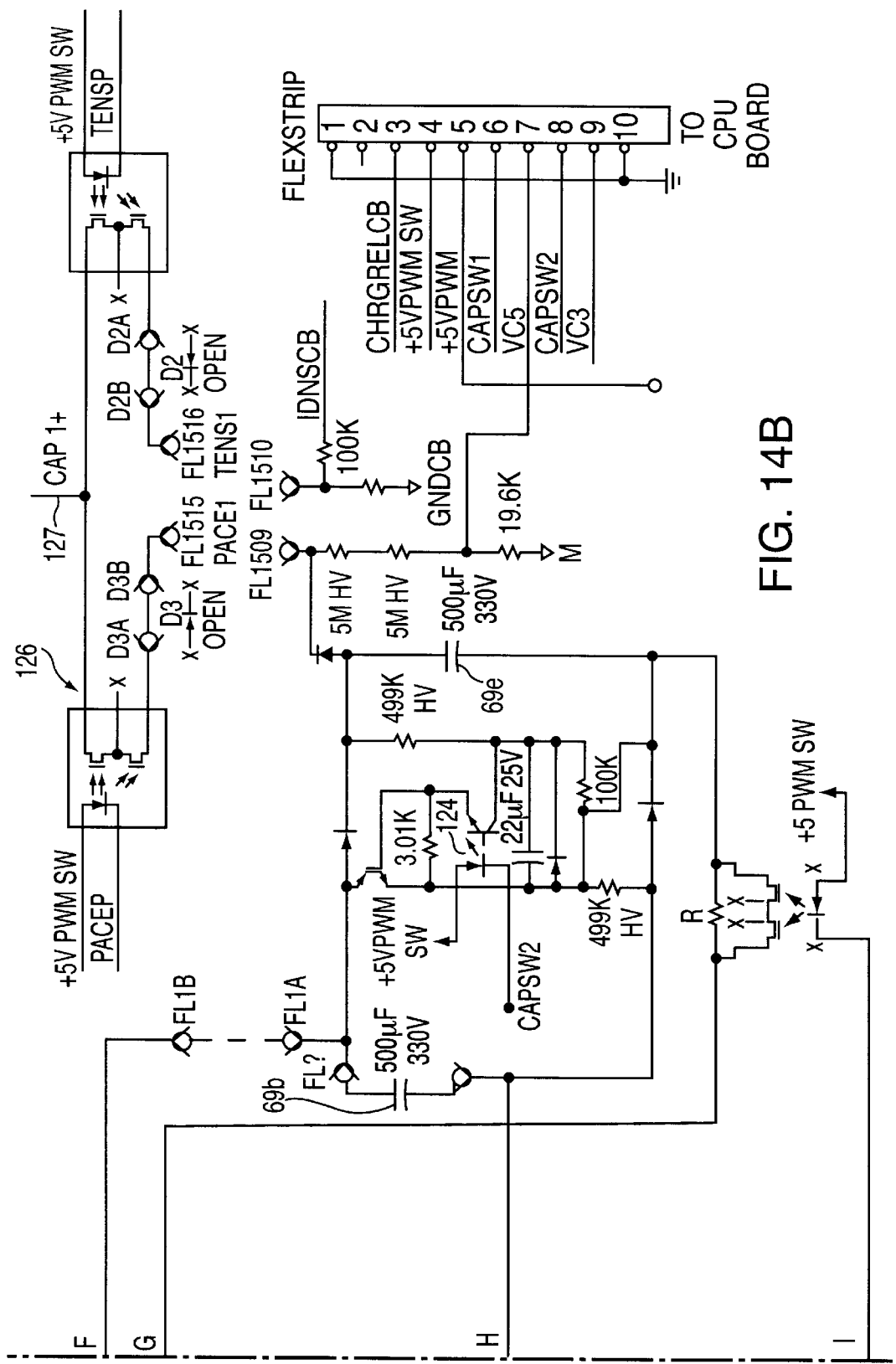
Figure 14C:
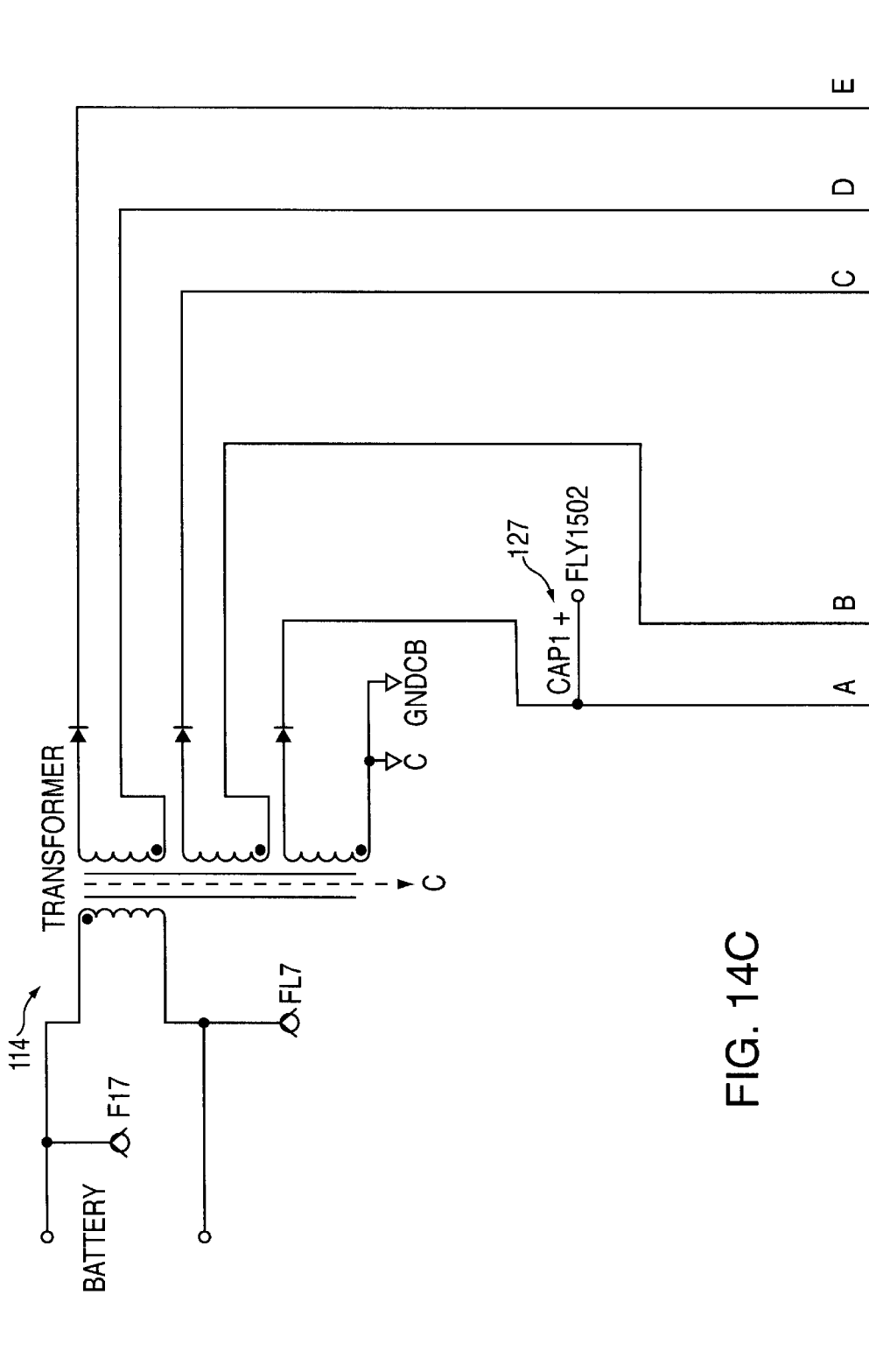

As noted above, outputs from control FPGA 110, namely CAPSW1 and CAPSW2, control switching of capacitors 69 from the 11111 configuration into the 2111 and 221 configurations. FIGS. 14A–14C shows a detailed circuit diagram of capacitors 69 (and of transformer 114). In preferred embodiments of the invention, the circuitry shown in FIGS. 14A–14C fits on a circuit board having a surface area of roughly 2 inches$^2$ or less. As shown in FIG. 14A, capacitors 69a, 69b, 69c, 69d and 69e are charged by power supply 20 (shown in FIG. 17) via transformer 114 (shown in FIG. 14C). CAPSW1 controls switching of capacitors 69b and 69c via transistor switch 122 (FIG. 14A), whereas CAPSW2 controls switching of capacitors 69d and 69e via transistor switch 124 (FIG. 14B). As noted above, this switching controls the overall, combined capacitance of 69a, 69b, 69c, 69d and 69e, which affects the amplitude and the tilt of a waveform output therefrom. Additional signal conditioning and output circuitry is also shown in FIGS. 14A–C but, since this particular circuitry is not essential to the invention, a detailed description thereof has been omitted for the sake of brevity.

It is worth noting, however, that FIGS. 14A,B also shows circuitry 126 which is used to output tactile stimulation and pacing signals from capacitor 69a. As shown in FIG. 14A, PACEP and TENSP, which are output by control FPGA 110, control application of the pacing and tactile stimulation and signals, respectively, from capacitor 69a. That is, charge from capacitor 69a, namely CAP1+127, is applied to circuitry 126 (FIG. 14B) and processed for output as the pacing or tactile stimulation signal. FIG. 14A also shows the CHARGELCB signal, which was described above, and ISNSCB and IDSNSCB signals. The ISNSCB signal comprises a current sense signal which is used to determine the charge of capacitors 69, whereas the IDSNSCB signal is used to determine the defibrillation energy current. This information is passed back to processor board 91, which processes this information and responds in the manner described above. For example, in the event that processor 109 determines that capacitors 69 are charged excessively for a particular patient such that over-current or even over-time defibrillation could occur, defibrillator 10 may be shut down or temporarily disabled so that capacitors 69 can be discharged without harm to the patient.

Returning to FIG. 13, output circuitry 117 includes signal conditioning circuitry as well as control circuitry which ensures that defibrillation energy will not be output inadvertently. In this regard, the invention also includes other safety features which limit transmission of the defibrillation control signal. For example, prior to delivery of the defibrillation energy, processor 109 monitors and demonstrates that state control clocks controlling the defibrillation energy are operational, and also tests the hardware components in order to detect any single point failures therein. These tests include testing switches in input circuitry 116, through which the defibrillation energy is transmitted. These switches are tested, one at a time, to demonstrate that each switch is capable of holding, off a full magnitude of the defibrillation energy. At each step of this switch test, a voltage across each transistor (i.e., switch) is monitored to record a test voltage and to record a transistor gate drive time constant in addition to combined opto isolator and transistor turn-off times. These voltages are then used to measure patient voltage during application of the defibrillation energy. Upper transistor switches, through which the defibrillation energy is transmitted, are tested first, followed by lower transistor switches. Each transistor switch is monitored and tested to demonstrate that the defibrillation energy would be terminated independently of hardware control timing.

In addition, as noted above, two pre-conditions must be met before defibrillation energy is transmitted the patient, namely, (i) the patient has experienced a treatable rhythm and (ii) the patient is unconscious. When these two conditions occur, processor 109 arms the defibrillation controller, e.g., control FPGA 110. Specifically, processor 109 provides the following sequence of control signals to initiate arming of the defibrillation controller. First, processor 109 tests its own internal safety signal ("PD_SAFE") to demonstrate its ability to override any hardware defibrillation control signals. Processor 109 then confirms that defibrillation energy can be detected properly by activating test signals and reading current feedback signals based on these test signals. Master control module 90, executing within processor 109, sets a "defibrillator arm request status" bit in memory for use and checking by an executive control module (not shown). This executive control module monitors operation of the software and updates a watchdog timer in processor 109 (which outputs the WATCHDOG_OUT signal noted above) when the software is confirmed to function properly. The executive control module then sets an arm request signal in the defibrillation controller and calls a watchdog update subroutine-which transitions the signal output from the watchdog timer. This causes a watchdog timer update and transitions the "armed request" status to the "armed" status in the defibrillation controller. The PD_SAFE signal is then put in the active state to allow the activation of hardware control signals for defibrillation therapy.

Next, processor 109 provides a final synchronized trigger signal to the defibrillation controller for delivery of the defibrillation energy. This synchronized trigger signal will be accepted only after the "armed" status has been established. The defibrillation controller will clear the armed status if the synchronization trigger signal is not provided within a 500 msec time period, thereby providing a limited acceptable period for defibrillation therapy. In a case that the defibrillation energy is transmitted to the patient, following transmission thereof, processor 109 determines if the defibrillation energy was transmitted properly. In this regard, defibrillation energy dosage errors of over-current are protected by the reset/watchdog circuit described above, but, if such an event does inadvertently occur, a fault condition is retained in a hardware fault register. Similarly, under-dosages of the defibrillation energy are also detected and stored. In addition to being stored, these and other defibrillator operational errors may be transmitted to base station 2.

Diagnostics module 84 also performs a plurality of diagnostics on defibrillator 10 to test defibrillator 10's hardware. These diagnostics include cold start diagnostics, which are executed when defibrillator 10 powers-up normally, warm start diagnostics which are executed when defibrillator 10 experiences transient reset or power loss, runtime diagnostics which are continuing, periodic tests performed in the background of normal operating conditions, and specific conditions diagnostics which are tests that are performed prior to, or when certain operations are performed, such as transmission of defibrillation energy.

Cold start diagnostics include RAM test, ROM test, D/A and A/D converter tests, FPGA tests, RTC and ECG sampling rate tests, LCD tests, voice circuitry tests, backup battery voltage tests, primary power supply voltage tests, internal voltage tests, old electrode harness test (i.e., whether the electrode harness has been changed after transmission of defibrillation energy), safety tests so as to verify that safety controls are operational, watchdog timer tests, shutdown tests, and patient parameters validation. Warm start diagnostics include operational state data tests (protected RAM validation) and patient parameters validation. Runtime diagnostics include watchdog timer active tests so as to confirm that a clock signal is active, software clock to real time clock comparison tests, software execution times checks, system voltage tests so as to test if the system is within voltage specifications, A/D runtime reference voltage tests, backup battery voltage tests, primary power supply voltage tests, internal voltage tests, old electrode harness test, operational state data integrity test, operational temperature tests, lead off tests, stuck keys test, safety tests including electrode harness time limit tests, defibrillation capacitor voltage tests, defibrillation output circuitry tests, output voltage tests, patient parameter validation, and impedance measurements. Specific conditions diagnostics include tests which are performed prior to transmission of defibrillation energy to the patient. These tests include cross checking processor tests whereby control FPGA 110 checks processor 109 for correct performance of a command sequence, and processor 109 checks control FPGA 110 for correct progression of states during set-up and transmission of defibrillation energy. Other tests include a watchdog timer test which resets the system in a case that processor 109 fails to respond periodically, electrodes-off tests in which processor 109 confirms that electrodes are attached to the patient, operational therapy state data integrity tests, pretherapy dosage tests whereby energy to be transmitted as defibrillation energy is compared with two impedance measurements prior to transmission, stuck ECG relay contacts tests (prior to defibrillation), H-bridge therapy tests, and delivered defibrillation current limiting tests.

Base Station

In brief, a base station for use with the present invention includes a defibrillator interface, over which information is exchanged with the defibrillator, and an external interface over which information is exchanged with an external entity, such as central repository 9, a doctor's office, a hospital, etc. Also included in the base station is a controller which receives patient information and defibrillation information from the defibrillator, transmits the patient information and defibrillation information to the external entity, receives defibrillator programming information from the external entity, programs the defibrillator in accordance with the defibrillator programming information, performs diagnostics on the defibrillator, and transmits results of the diagnostics to at least one of the defibrillator and the external entity. Communication between the defibrillator and the base station may be via an RF, IR, or direct electrical connection. In addition, communication/testing may be effected by direct contact between the sensing electrodes and the base station.

Figure 15:
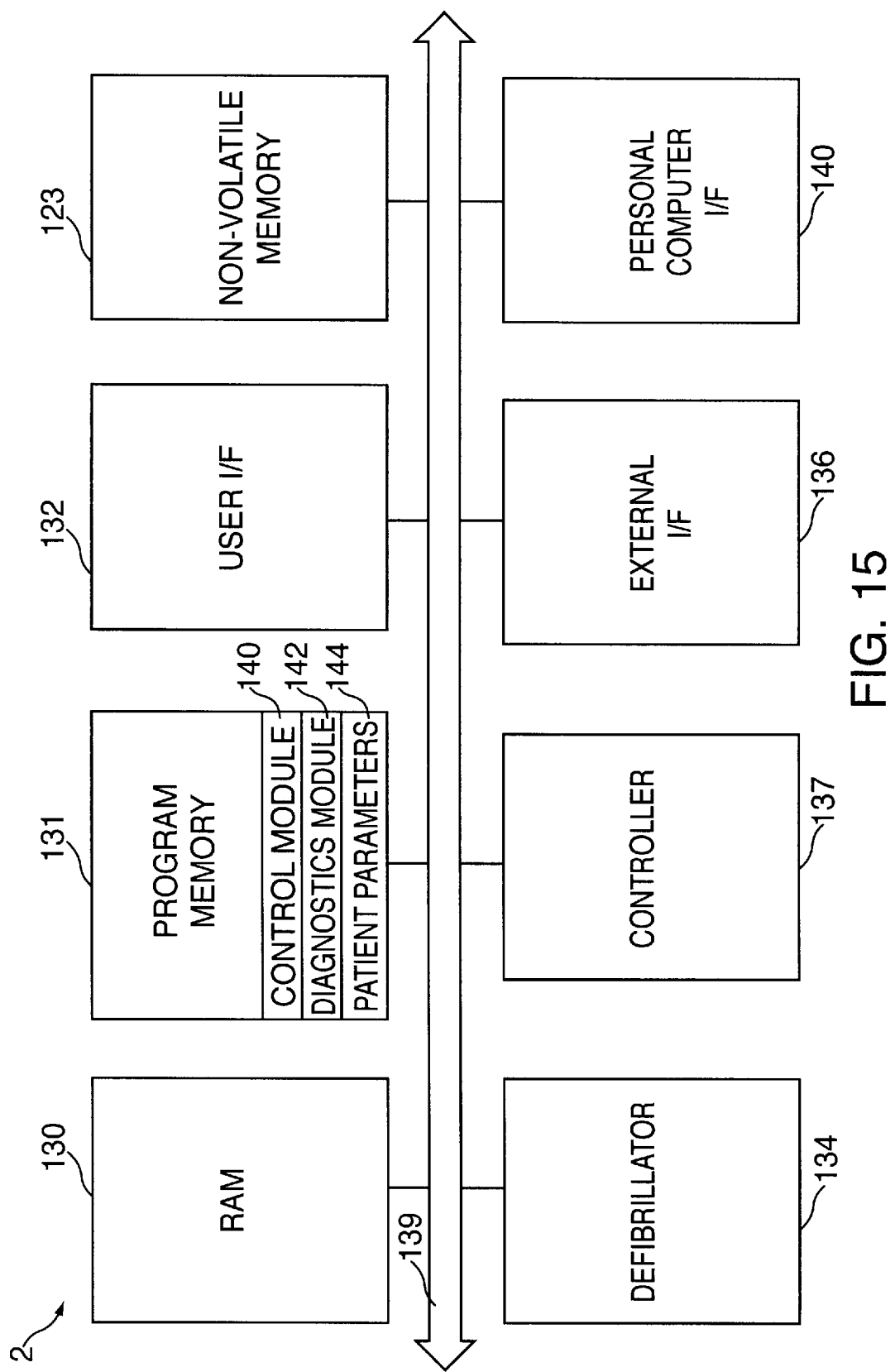
FIG. 15 is a block diagram of a base station used in the system of FIGS. 1 and 2.

A block diagram of base station 2 is shown in FIG. 15. As shown, base station 2 includes, RAM 130, program memory 131, user interface 132, non-volatile memory 133, defibrillator interface 134, external interface 136, controller 137, address/data bus 139, and personal computer interface 140. Base station 2 may receive power from an external source, such as a wall outlet, or from a battery (not shown). Each of the features of base station 2 shown in FIG. 15 is described in more detail below.

User interface 132 can comprise a keyboard, buttons, switches, or the like, which provide a user with a way to control base station 2 directly. Defibrillator interface 134 corresponds to connector 51 shown in FIG. 1 and comprises an interface to defibrillator 10, over which patient information (e.g., ECG information) and defibrillator information (e.g., errors in operation of defibrillator 10) is received from the defibrillator, and over which external information (i.e., information received from an external source, such as new patient parameters) is transmitted to the defibrillator. Defibrillator interface 134 includes base station 2's physical connector ID. Defibrillator interface 134 is preferably a serial interface and, as described above, mates to the same connector on defibrillator 10 that is used to interface defibrillator 10 to electrode harness 4.

Personal computer 6, which is interfaced to base station 2 via personal computer interface 140, may be used to indicate operational characteristics of base station 2, such as when base station 2 is uploading data, whether that upload was successful, a display of all uploaded data, etc.

External interface comprises a link to an external location, such as central repository 9 (see FIG. 1) or a personal computer, over which patient and defibrillation information is transmitted to the external source, and over which the external information is received from the external source. External interface can comprise a modem link, a network connection, or the like, over which data may be transmitted to and from base station 2. At this point, it is noted that all information stored in data logging memory block 57 above can be transmitted over defibrillator interface 134 and external interface 136 of base station 2.

Controller 137 comprises a microprocessor or the like, which is capable of executing stored program instructions so as to control operation of base station 2. Any type of processor may be employed, such as those described above with respect to defibrillator 10. Program instructions that can be executed by controller 137 are stored in program memory 131. Program memory 131 preferably comprises an EPROM, or the like, which can be reprogrammed with newly-received information or routines by controller 137. In preferred embodiments of the invention, program memory 131 stores control module 140, diagnostics module 142, and patient parameters 144, among other data and software modules.

Patient parameters 144 correspond to the patient parameters described above and, as noted, can be reprogrammed based on information, such as instructions, provided from an external source. Control module 140 is executed so as to control transfer of information between defibrillator 10, base station 2, and central repository 9. Diagnostics module 142 comprises a module which performs various safety diagnostics on defibrillator 10 when defibrillator 10 is interfaced to base station 2. By way of example, control module 140 may be executed to retrieve information relating to operational errors of defibrillator 10 from data logging memory block 57 of defibrillator 10. Diagnostics module 142 may then use this information to target-test components and/or software on defibrillator 10 that may be responsible for these errors. Alternatively, diagnostics module 142 may perform a complete safety diagnostic check on all aspects of defibrillator 10 each time defibrillator 10 is mated to base station 2.

In this regard, base station 2 is capable of performing diagnostics comprising an audio test to confirm that messages and tones output by defibrillator 10 are clearly audible; measurement tests to confirm that all measurements in defibrillator 10 needed to perform a defibrillation procedure are as expected; ECG analysis tests so as to confirm that defibrillator 10 is able to detect and differentiate various cardiac arrhythmias; defibrillation waveform tests so as to confirm that defibrillator 10 can generate and output a waveform appropriate for a patient having a particular impedance; patient leakage current tests so as to confirm that leakage current in defibrillator 10 is not above an acceptable level; over-dosage defibrillation tests so as to confirm that defibrillator 10 will automatically terminate an over-current defibrillation (e.g., $I_{max} \geq 30$ A) and an over-time defibrillation (e.g., $t_{max} \geq 20$ msec); under-dosage defibrillation tests so as to determine if defibrillator is providing an under-current defibrillation (e.g., $I_{max}$ is less than a required current for a patient's impedance measurement by more than 20%) or an under-time defibrillation (e.g., $t_{max}$ is less than a required duration for a patient's impedance measurement by more than 20%); power consumption tests so to confirm that defibrillator 10 meets with the power requirements set forth in Table 2 below; and button switch tests to confirm that each button on user interface 47 is operating properly.

TABLE 2

| Defibrillator Operating Conditions | Current Constraint |
| --- | --- |
| Low-Power Mode | <2 mA |
| Patient Monitoring Only | <20 mA |
| Detection of Ventricular Fibrillation | <400 mA |
| When any of the following operations are active | <900 mA |
| i) Flash read/write | |
| ii) LCD | |
| iii) Voice message/Tone | |
| iv) Accessory Communications | |
| Charging of Capacitors | <3.0 A |

Diagnostics module 142 may also be executed to check proper transmission of patient parameters or other programming information from base station 2 to defibrillator 10. More specifically, in operation, base station 2 receives new patient parameters over external interface 136 from central repository 9, and transmits these patient parameters over defibrillator interface 134 to data logging memory block 57 in defibrillator 10. Diagnostics module 142 may then be executed to issue a request for the patient parameters stored in data logging memory block 57 over defibrillator interface 134, to receive the patient parameters therefrom over defibrillator interface 134, and to compare the patient parameters, including a checksum, to the same patient parameters, which are stored in program memory 131, so as to verify valid receipt of the patient parameters by defibrillator 10.

In preferred embodiments of the invention, the results of the foregoing diagnostics may be transmitted back to defibrillator 10 in order to warn the user of the defects via, e.g., an LCD or a speaker. In addition, the results of such diagnostics may also be transmitted to an external location via external interface 136 for analysis or the like.

Base station 2 also includes RAM 130, out of which controller 137 executes program instructions stored in program memory 131, and non-volatile memory 133, which stores information received from defibrillator 10 and from an external source. Non-volatile memory 133 can comprise an NVRAM, battery backed-up RAM, EPROM, or the like, and has a storage capacity which is the same as or greater than that of data logging memory block 57 on defibrillator 10. This is preferable, since non-volatile memory 133 should be capable of storing any information downloaded to base station 2 from defibrillator 10, including all or part of the information described above that is stored in data logging memory block 57, i.e., abnormal heart activity of the patient, the patient's ECG before, during and after application of defibrillation energy, etc. In this regard, upon connection of defibrillator 10 to defibrillator interface 134, in preferred embodiments of the invention, controller 137 requests defibrillator 10 to upload data stored in data logging memory block 57 and, if the data has been uploaded successfully, controller 137 requests defibrillator 10 to reset all recorded data in data logging memory block 57, and also to clear patient parameters stored therein to their default settings.

As noted above, it is possible to reprogram defibrillator 10 and/or base station 2 with information received from the external location. In fact, it is even possible to use information received from defibrillator 10 to affect such reprogramming. More specifically, information relating to patients using the same type of defibrillator, i.e., defibrillator 10's type, is stored in central repository 9. This information can be analyzed in order to test algorithms used in defibrillator 10. One such algorithm that may be tested is an algorithm used by ECG analysis module 87 above to detect irregular heart activity. Once this algorithm is tested based on analysis results from plural defibrillators, it is possible to pinpoint errors in the algorithm, and to correct these errors. Thereafter, the corrected algorithm can be transmitted back to base station 2, as well as to a plurality of other base stations. In this regard, central repository may identify base station 2 as corresponding to defibrillator 10 based on defibrillator 10's ID number. Base station 2 can then reprogram defibrillator 10 using the corrected algorithm. As a result the invention provides a means by which to improve its performance based on information collected thereby.

The present invention has been described with respect to particular illustrative embodiments. It is to be understood that the invention is not limited to the above-described embodiments and modifications thereto, and that various changes and modifications may be made by those of ordinary skill in the art without departing from the spirit and scope of the appended claims.

What is claimed is:

1. A defibrillator for delivering defibrillation energy to a patient, the defibrillator comprising:
    a patient interface, over which patient information is received from the patient, and over which the defibrillation energy is transmitted to the patient; and
    a processor which operates in a normal mode and a low-power consumption mode, wherein, during the normal mode, the processor receives the patient information and controls transmission of the defibrillation energy in accordance with the patient information; and wherein said processor enters into said low-power consumption mode periodically for variable periods of time, said time periods being selected by the processor based on information specific to the patient.

2. The defibrillator of claim 1 wherein said patient classified as being one of a high and a low risk patient, and wherein said processor selects a time period for low-power consumption mode that is longer if the patient is a low risk patient then if the patient is a high risk patient.

3. The defibrillator of claim 2 wherein said processor is adapted to eliminate said low-power consumption mode if the patient is a high risk patient.

4. The defibrillator of claim 1 wherein said processor analyzes the patient information from the patient interface and determines if the patient is a low risk patient or a high risk patient.

5. The defibrillator of claim 4 wherein said processor classifies the patient based on at least one of the patient's EGG and the patient's prior history.

6. The defibrillator of claim 1 further comprising an external interface and wherein said processor receives data from said external interface indicating whether the patient is a low-risk patient or a high-risk patient.

7. A defibrillator according to claim 1, further comprising a user interface by which a user may place the processor in the normal mode manually.

8. A defibrillator according to claim 1, further comprising a plurality of hardware components for use in outputting the defibrillation energy and for communicating with the patient;
    wherein the processor causes each of the plurality of hardware components to be selectively powered-up and powered-down at predetermined time intervals.

9. A defibrillator according to claim 1 wherein said processor and patient interface are disposed in a housing, said housing being constructed and arranged to be worn by the patient.

10. An external defibrillator adapted to provide cardiac therapy to a patient classified as either a high risk or a low risk patient for cardiac arrhythmia, comprising:
    sensing circuitry adapted to sense intrinsic activity of the patient;
    pulse generating circuitry adapted to generate pulses to be applied to the patient in response to commands;
    a processor adapted to receive information from said sensing circuitry about said intrinsic activity and to generate, in response to said information, said commands, said processor having a normal mode of operation during which said processor receives said information and generates said commands and a low power mode in which said processor does not generate commands, wherein said processor determinations a duration of said normal and said low mode in accordance with the classification of the patient.

11. The defibrillator of claim 10 wherein said processor is adapted to determine the patient's classification based on said information.

12. The defibrillator if claim 10 wherein said processor is adapted to determine the patient's classification based on a prior history of a patient.

13. The defibrillator of claim 10 wherein said processor operates in said low power mode for a longer period of time than in said normal mode if the patient's classification is low risk.

14. The defibrillator of claim 10 wherein said processor is adapted to operate in said low power mode for a shorter period than in said normal mode if the patient's classification is determined to be high risk.

15. The defibrillator of claim 10 wherein the patient can further be classified as being very high risk and wherein said processor is adapted to operate only in said normal mode if the patient classification is determined to be very high risk.

16. The defibrillator of claim 10 wherein said processor is operable in a deep low power mode during which a set of elementary routines are performed and a light low power in which more routines are performed.

17. The defibrillator of claim 16 wherein said processor consumes less power in said light low power mode then in said normal mode.

18. The defibrillator of claim 16 wherein said processor is operated in said deep low power mode when said information indicates benign cardiac rhythms for a predetermined time period.

19. The defibrillator of claim 16 wherein said processor is operated in said light low power mode for a predetermined period after a treatable rhythm has occurred.

20. The defibrillator of claim 10 wherein said processor is switched from said low power mode to said normal mode at predetermined time intervals.

21. The defibrillator of claim 10 further comprising a manual button and wherein said processor is switched from said low power mode to said normal mode in response to an activation of said manual button.

22. A defibrillator according to claim 21, further comprising a memory which stores a log of the patient information for a span of time; wherein the processor varies the predetermined periods based on the log of patient information stored in the memory.

23. An external defibrillator adapted to provide cardiac therapy to a patient, comprising:
    sensing circuitry adapted to sense intrinsic activity of the patient;
    pulse generating circuitry adapted to generate pulses to be applied to the patient in response to commands;
    a processor adapted to receive information from said sensing circuitry about said intrinsic activity and to generate, in response to said information, said commands, said processor having a normal mode of operation during which said processor receives said information and generates said commands and a low power mode in which said processor does not generate commands, wherein said processor is switched between said normal and said low mode in accordance with a cardiac condition of the patient;

wherein in said processor operates 50% of the time in said normal mode.

24. The defibrillator of claim 23 wherein said processor operates in said normal mode for about 4 msec before switching to said low power mode.

25. An external defibrillator adapted to provide cardiac therapy to a patient, comprising:

sensing circuitry adapted to sense intrinsic activity of the patient;

pulse generating circuitry adapted to generate pulses to be applied to the patient in response to commands;

a processor adapted to receive information from said sensing circuitry about said intrinsic activity and to generate, in response to said information, said commands, said processor having a normal mode of operation during which said processor receives said information and generates said commands and a low power mode in which said processor does not generate commands, wherein said processor is switched between said normal and said low mode in accordance with a cardiac condition of the patient;

wherein said processor is switched from said low power mode to said normal mode at predetermined time intervals.

* * * * *